(12) United States Patent
Tsien et al.

(10) Patent No.: US 6,472,541 B2
(45) Date of Patent: Oct. 29, 2002

(54) PROTECTING GROUPS WITH INCREASED PHOTOSENSITIVITIES

(75) Inventors: Roger Y. Tsien, La Jolla, CA (US); Toshiaki Furuta, Chiba (JP)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/197,294

(22) Filed: Nov. 20, 1998

(65) Prior Publication Data

US 2002/0016472 A1 Feb. 7, 2002

(51) Int. Cl.[7] .............................................. C07D 311/02
(52) U.S. Cl. ..................... 549/283; 536/1.11; 536/17.3; 436/71; 530/300; 546/152; 546/153
(58) Field of Search ..................... 549/283; 536/1.11, 536/17.3; 436/71; 530/300; 546/152, 153

(56) References Cited

U.S. PATENT DOCUMENTS

| 5,082,952 A | 1/1992 | Meier ............................. 549/3 |
| 5,187,049 A | 2/1993 | Sher et al. ................... 430/340 |
| 5,721,355 A | 2/1998 | Brush ....................... 536/25.32 |

OTHER PUBLICATIONS

Baranowska et al., J. Label. Comp. & Radiopharm. vol. XXIX, No. 12 pp. 1301–1307, Jul. 1991.*

* cited by examiner

*Primary Examiner*—Bennett Celsa
(74) *Attorney, Agent, or Firm*—Knobbe, Martens, Olson, & Bear LLP

(57) ABSTRACT

Protecting groups derived from a halogenated coumarin group, a quinoline-2-one group, a xanthene group, a thioxanthene group, a selenoxanthene group, or an anthracene group are described. The protecting groups is photolabile and can be removed by irradiating the group with light, such as flash photolysis with ultraviolet radiation or pulsed infrared radiation.

19 Claims, 1 Drawing Sheet

PROTECTING GROUPS WITH INCREASED PHOTOSENSITIVITIES

STATEMENT AS TO FEDERALLY SPONSORED RESEARCH

This invention was made with Government support under Grant (or Contract) No. NS27177, awarded by the National Institutes of Health. The Government has certain rights in this invention.

BACKGROUND OF THE INVENTION

The invention relates to protecting groups that can be removed by irradiation.

Protecting groups can be used to mask compounds, or portions of compounds, from interacting in chemical or biological systems. For example, a protecting group can prevent a compound from undergoing a chemical reaction by changing the chemical nature of a functionality. In another example, a protecting group can mask or conceal a biological response induced by the compound in a biological system, both in vivo and in vitro (e.g., in a cell, a tissue, or an assay). One class of protecting group of particular interest for use in biological systems are photolabile protecting groups. Photolabile protecting groups, sometimes called caging groups, have become a mainstay of organic synthesis, biotechnology, and cell biology, because cleavage by light is a very mild deprotection step that is usually orthogonal to other experimental manipulations. The outstanding spatial and temporal precision with which light can be controlled enables diverse applications such as photolithographic construction of complex peptide and oligonucleotide arrays, or physiological release ("uncaging") of bioactive substances in cells and tissues. Examples of caging groups that can be removed from a compound by exposing the compound to light, for example, by a flash of UV, are described in Adams, S. R. and Tsien, R. Y. *Annual Rev. Physiology* 55:755–784 (1993), incorporated herein by reference.

In general, the protecting groups mask charged (e.g., carboxylate or phosphate) or polar (e.g., amine, sulfhydryl, or hydroxyl) functionalities of the compounds, which can increase their hydrophobicity and their membrane permeability. Before photolysis, these caged compounds are biologically or chemically inactive because at least one of the key functionalities is blocked. The activity of the molecule can be triggered by a pulse of light, which releases the protecting group. In this way, photolabile protecting groups can be removed from a protected compound by irradiation to control release of the compound both spatially and temporally. In particular, compounds of biologically active products can be used to probe biological effects of the compounds. While uncaging can take place in a sample, such as a solution, a tissue sample, or in live cells, this strategy is very valuable for in vivo biological application. It allows control of the onset of bioactivity in living cells with millisecond temporal precision.

Examples of photolabile protecting groups that have been used to cage biomolecules include 2-nitrobenzyl, 1-(2-nitrophenyl)ethyl, 4,5-dimethoxy-2-nitrobenzyl, and -carboxy-4,5-dimethoxy-2-nitrobenzyl. The mechanism of photo-deprotection of caging groups and the applications of caging compounds have been reviewed. See, for example, McCray, J. A. and Trentham, D. R., *Annu. Rev. Biophys. Biophys. Chem.*, 18:239–270 (1989), and Adams, S. R. and Tsien, R. Y., *Annu. Rev. Physiol.* 55:755–784 (1993). Examples of caged molecules which have had successful applications in biology include caged cAMP (see, e.g., Walker, J. W., et al., *Methods Enzymol.* 172:288–301 (1989), and Wootton, J. F. and Trentham, D. R., *NATO ASI Ser. C* 272 (1989)), caged nitric oxide (see, e.g., Lev-Ram, V., et al., *Neuron* 15:407–415 (1995), and Makings, L. R. and Tsien, R. Y., *J. Biol. Chem.* 269:6282–6285 (1994)), caged fluorescein (see, e.g., Krafft, G. A., et al., *J. Am. Chem. Soc.* 110:301 (1988)), caged calcium (see, e.g., Adams, S. R., et al., *J. Am. Chem. Soc.* 110:3212 (1988), and Tsien, R. Y. and Zucker, R. S., *Biophys. J.* 50:843–853 (1986)), caged glutamate (see, e.g., Callaway, E. M. and Katz, L. C., *Proc. Natl. Acad. Sci. U.S.A.* 90:7661–7665 (1993), Wilcox, M., et al., *J. Org. Chem.* 55:1585 (1990), and Corrie, J. E., et al., *J. Physiol. (Lond)* 465:1–8 (1993)), and caged inositol-1,4,5-triphosphate ($IP_3$) (see, e.g., Walker, J. W., et al., *Nature* 327:249–252 (1987)).

SUMMARY OF THE INVENTION

In general, the invention features a protecting group derived from a halogenated coumarin group, a quinoline-2-one group, a xanthene group, a thioxanthene group, a selenoxanthene group, or an anthracene group. The protecting group is photolabile and can be removed by irradiating the group with light, such as flash photolysis with ultraviolet radiation or pulsed infrared radiation.

In one aspect, the invention features a protecting group derived from a halogenated coumarin or quinoline-2-one group. The protecting group can be a part of a compound. The compound has the formula:

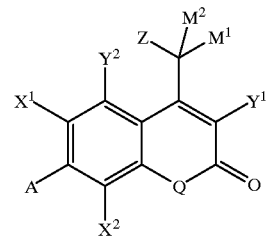

In the formula: A is —OH, substituted or unsubstituted alkoxy, —OC(O)$CH_3$, —$NH_2$, or —$NHCH_3$; each of $X^1$ and $X^2$, independently, is H, Cl, Br, or I, at least one of $X^1$ and $X^2$ being Cl, Br, or I, Q is —O—, —NH—, or —$NCH_3$—; $Y^1$ is —H, —Cl, —Br, —I, —C(O)OH, —$NO_2$, —C(O)$NHR^1$, —CN, —C(O)H, —C(O)$CH_3$, benzoxazol-2-yl, benzothiazol-2-yl, or benzimidazol-2-yl; $Y^2$ is —H, —C(O)OH, or —$SO_3H$; $M^1$ is —H, —$CH_3$, —$NR^2R^3$, —C(O)$NR^2R^3$, or —COOH; Z is a leaving group and $M^2$ is —H, or Z and $M^2$ together are =$N_2$, =O, or =$NNHR^1$; and each of $R^1$, $R^2$, and $R^3$, independently, is a substituted or unsubstituted moiety selected from the group consisting of a $C_{1-20}$ alkyl, a $C_{2-20}$ alkenyl, a $C_{2-20}$ alkynyl, a $C_{1-20}$ alkoxy, a $C_{1-20}$ thioalkoxy, a $C_{1-20}$ alkylsulfonyl, a $C_{4-16}$ arylsulfonyl, a $C_{2-20}$ heteroalkyl, a $C_{2-20}$ heteroalkenyl, a $C_{3-8}$ cycloalkyl, a $C_{3-8}$ cycloalkenyl, a $C_{4-16}$ aryl, a $C_{4-16}$ heteroaryl, and a $C_{2-30}$ heterocyclyl. The compound can be a salt.

In another aspect, the invention features a protecting group derived from a xanthene group, a thioxanthene group, a selenoxanthene group, or an anthracene group. The protecting group can be a part of a compound. The compound has the formula:

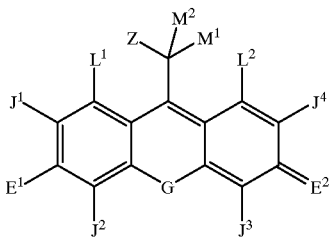

In the formula: $E^1$ is —OH, substituted or unsubstituted alkoxy, —OC(O)CH$_3$, —NH$_2$, —NHCH$_3$, or —N(CH$_3$)$_2$; $E^2$ is =O, =NH$_2^+$, =NHCH$_3^+$, or =N(CH$_3$)$_2^+$; G is O, S, SO$_2$, Se, or C(CH$_3$)$_2$; each of $J^1$, $J^2$, $J^3$, and $J^4$, independently, is H, F, Cl, Br, or I; each of $L^1$ and $L^2$, independently, is H, —C(O)OH, or —SO$_3$H; $M^1$ is —H, —CH$_3$, substituted amino, disubstituted amino, amido, —COOH, substituted or unsubstituted $C_{1-20}$ alkyl, substituted or unsubstituted $C_{2-20}$ heteroalkyl, or substituted or unsubstituted $C_{2-30}$ heterocyclyl; Z is a leaving group and $M^2$ is —H, or Z and $M^2$ together are =N$_2$, =O, or =NNHR$^1$; and R$^1$ is a substituted or unsubstituted moiety selected from the group consisting of a $C_{1-20}$ alkyl, a $C_{2-20}$ alkenyl, a $C_{2-20}$ alkynyl, a $C_{1-20}$ alkoxy, a $C_{1-20}$ thioalkoxy, a $C_{1-20}$ alkylsulfonyl, a $C_{4-16}$ arylsulfonyl, a $C_{2-20}$ heteroalkyl, a $C_{2-20}$ heteroalkenyl, a $C_{3-8}$ cycloalkyl, a $C_{3-8}$ cycloalkenyl, a $C_{4-16}$ aryl, a $C_{4-16}$ heteroaryl, and a $C_{2-30}$ heterocyclyl. The compound can be a salt.

In preferred embodiments, Z and $M^2$ together are =N$_2$, =O, or =NNHR$^1$. In other preferred embodiments, Z is a leaving group and $M^2$ is —H.

A leaving group is a group that can be photolytically displaced. Generally, a leaving group departs from a substrate with the pair of electrons of the covalent bond between the leaving group and the substrate. Preferred leaving groups stabilize the pair of electrons via the presence of electron withdrawing groups, aromaticity, resonance structures, or a combination thereof. Examples of leaving groups include halide, or moieties linked by a carboxylate, a carbonate, an amide, a carbamate, a phosphate, a sulfonate, an amino, an aryloxide, or a thiolate group.

When Z is a leaving group, Z can be a halogen, —OC(O)R$^4$, —OP(O)R$^5$R$^6$, —OP(O)(OH) R$^5$, —OC(O)NR$^5$R$^6$, —NR$^5$C(O)OR$^6$, —SR$^4$, alkoxy, aryloxy, —NR$^5$R$^5$, —NR$^5$C(O)R$^6$, —O$_3$SR$^4$, or —O—NN(O)(NR$^5$R$^6$). Each of R$^4$, R$^5$, and R$^6$, independently, can be a substituted or unsubstituted moiety selected from the group consisting of a $C_{1-20}$ alkyl, a $C_{2-20}$ alkenyl, a $C_{2-20}$ alkynyl, a $C_{1-20}$ alkoxy, a $C_{1-20}$ thioalkoxy, a $C_{1-20}$ alkylsulfonyl, a $C_{4-16}$ arylsulfonyl, a $C_{2-20}$ heteroalkyl, a $C_{2-20}$ heteroalkenyl, a $C_{3-8}$ cycloalkyl, a $C_{3-8}$ cycloalkenyl, a $C_{4-16}$ aryl, a $C_{4-16}$ heteroaryl, a $C_{2-30}$ heterocyclyl, a cyclitol radical, a saccharide radical, a saccharide phosphate radical, a polysaccharide radical, a lipid radical, an amino acid radical, a peptide radical, a nucleoside radical, a nucleotide radical, a nucleoside monophosphate radical, a nucleoside thiophosphate radical, a nucleoside triphosphate radical, a nucleoside diphosphate radical, and a polynucleotide radical. Alternatively, R$^5$ and R$^6$, together, can form a substituted or unsubstituted moiety selected from the group consisting of a $C_{1-20}$ alkylene, a cyclitol diradical, a saccharide diradical, a saccharide phosphate diradical, a polysaccharide diradical, a lipid diradical, an amino acid diradical, a peptide diradical, a nucleoside diradical, a nucleotide diradical, a nucleoside monophosphate diradical, a nucleoside thiophosphate diradical, a nucleoside diphosphate diradical, a nucleoside triphosphate diradical, or a polynucleotide diradical.

In preferred embodiments, when the protecting group is a derivative of a halogenated coumarin, Q is O, A is —OH, —OCH$_3$, or —OC$_2$H$_5$, X$^2$ is —H, Y$^2$ is —H, Y$^1$ is —H, Z is —Cl, —OC(O)O-(4-nitrophenyl), —NR$^5$C(O)R$^6$, —OC(O)NR$^5$R$^6$, or —OP(O)R$^5$R$^6$. In certain embodiments, R$^5$ can be H and R$^6$ can be an amino acid radical or a peptide radical, or R$^5$ and R$^6$, together, can form a nucleoside diradical.

In other preferred embodiments, when the protecting group is a xanthene derivative, $E^2$ is =O, G is O, and $M^1$ is H, each of $J^1$, $J^2$, $J^3$, and $J^4$ is H, $M^2$ is H, and Z is —Cl, —OC(O)R$^1$, or —OC(O)O-(4-nitrophenyl).

In another aspect, the invention features a method of deprotecting a compound. The method includes exposing a caged compound having a photolabile protecting group for a sufficient time to remove the photolabile protecting group and deprotect the compound. The caged compound has a two photon action cross section at 740 nm of at least $0.1 \times 10^{-50}$ cm$^4$s.

In another aspect, the invention features a method of deprotecting a compound. The method includes exposing a caged compound having a photolabile protecting group derived from a derived from a halogenated coumarin, a quinoline-2-one, a xanthene, a thioxanthene, a selenoxanthene, or an anthracene to a sufficient amount of radiation for a sufficient time to remove the photolabile protecting group and deprotect the compound.

In another aspect, the invention features a method for introducing a compound into a sample. The method includes the steps of contacting the sample with a caged compound having a photolabile protecting group derived from a halogenated coumarin, a quinoline-2-one, a xanthene, a thioxanthene, a selenoxanthene, or an anthracene, and exposing the caged compound to a sufficient amount of radiation for a sufficient time to remove the photolabile protecting group and deprotect the compound.

In another aspect, the invention features a method for introducing a compound into a sample. The method includes the steps of contacting the sample with a caged compound having a photolabile protecting group, and exposing the caged compound to a sufficient amount of radiation for a sufficient time to remove the photolabile protecting group and deprotect the compound. The caged compound has a two photon action cross section at 740 nm of at least $0.1 \times 10^{-50}$ cm$^4$s.

The sample can be a biological sample, a spatially arrayed combinatorial library, or an optical memory (e.g., a three dimensional optical memory).

The compound can have a one photon action cross section at 365 nm of at least 110 M$^{-1}$cm$^{-1}$ (e.g., at least 200 M$^{-1}$cm$^{-1}$, preferably at least 300 M$^{-1}$cm$^{-1}$). The compound can have a two photon action cross section at 740 nm of at least $0.1 \times 10^{-50}$ cm$^4$s/photon (e.g., at least $0.5 \times 10^{-50}$ cm$^4$s/photon, preferably at least $1.0 \times 10^{-50}$ cm$^4$s/photon). The compound can have a two photon action cross section at 800 nm of at least $0.05 \times 10^{-50}$ cm$^4$s/photon (e.g., at least $0.1 \times 10^{-50}$ cm$^4$s/photon, preferably at least $0.2 \times 10^{-50}$ cm$^4$s/photon).

The radiation can be ultraviolet radiation or infrared radiation (e.g., pulsed infrared radiation). The exposing step can be a two photon process.

The compound can have the formula Z-H. Z can be halogen, —OC(O)R$^4$, —OP(O)R$^5$R$^6$, —OP(O)(OH)R$^5$, —OC(O)NR$^5$R$^6$, —NR$^5$C(O)OR$^6$, —SR$^4$, alkoxy, aryloxy, —NR$^5$R$^5$, —NR$^5$C(O)R$^6$, or —O$_3$SR$^4$; and each of R$^4$, R$^5$, and R$^6$, independently, is a substituted or unsubstituted moiety selected from the group consisting of a C$_{1-20}$ alkyl, a C$_{2-20}$ alkenyl, a C$_{2-20}$ alkynyl, a C$_{1-20}$ alkoxy, a C$_{1-20}$ thioalkoxy, a C$_{2-20}$ heteroalkyl, a C$_{2-20}$ heteroalkenyl, a C$_{3-8}$ cycloalkyl, a C$_{3-8}$ cycloalkenyl, a C$_{4-16}$ aryl, a C$_{4-16}$ heteroaryl, a C$_{2-30}$ heterocyclyl, a cyclitol radical, a saccharide radical, a saccharide phosphate radical, a polysaccharide radical, a lipid radical, an amino acid radical, a peptide radical, a nucleoside radical, a nucleotide radical, a nucleoside monophosphate radical, a nucleoside thiophosphate radical, a nucleoside diphosphate radical, a nucleoside triphosphate radical, and a polynucleotide radical; or R$^5$ and R$^6$, together, form a substituted or unsubstituted moiety selected from the group consisting of a C$_{1-20}$ alkylene, a cyclitol diradical, a saccharide diradical, a saccharide phosphate diradical, a polysaccharide diradical, a lipid diradical, an amino acid diradical, a peptide diradical, a nucleoside diradical, a nucleotide diradical, a nucleoside monophosphate diradical, a nucleoside thiophosphate diradical, a nucleoside diphosphate diradical, a nucleoside diphosphate diradical or a polynucleotide diradical. The compound can be a salt.

The photolabile protecting group can have the formula

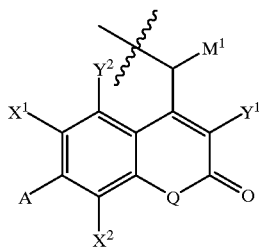

in which A is —OH, substituted or unsubstituted alkoxy, —OC(O)CH$_3$, —NH$_2$, or —NHCH$_3$; each of X$^1$ and X$^2$, independently, is H, Cl, Br, or I, at least one of X$^1$ and X$^2$ being Cl, Br, or I; Q is —O—, —NH—, or —NCH$_3$—; Y$^1$ is —H, —Cl, —Br, —I, —C(O)OH, —NO$_2$, —C(O)NHR$^1$, —CN, —C(O)H, —C(O)CH$_3$, benzoxazol-2-yl, benzothiazol-2-yl, or benzimidazol-2-yl; Y$^2$ is —H, —C(O)OH, or —SO$_3$H; M$^1$ is —H, —CH$_3$, —NR$^2$R$^3$, —C(O)NR$^2$R$^3$, or —COOH; and each of R$^1$, R$^2$, and R$^3$, independently, is a substituted or unsubstituted moiety selected from the group consisting of a C$_{1-20}$ alkyl, a C$_{2-20}$ alkenyl, a C$_{2-20}$ alkynyl, a C$_{1-20}$ alkoxy, a C$_{1-20}$ thioalkoxy, a C$_{1-20}$ alkylsulfonyl, a C$_{4-16}$ arylsulfonyl, a C$_{2-20}$ heteroalkyl, a C$_{2-20}$ heteroalkenyl, a C$_{3-8}$ cycloalkyl, a C$_{3-8}$ cycloalkenyl, a C$_{4-16}$ aryl, a C$_{4-16}$ heteroaryl, and a C$_{2-30}$ heterocyclyl.

Alternatively, the photolabile protecting group can have the formula

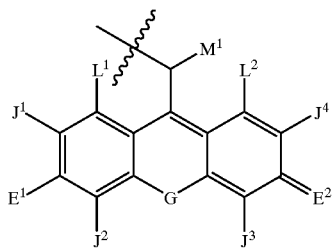

in which E$^1$ is —OH, —OCH$_3$, —OC$_2$H$_5$, —OC(O)CH$_3$, —NH$_2$, —NHCH$_3$, or —N(CH$_3$)$_2$; E$^2$ is =O, =NH$_2^+$, =NHCH$_3^+$, or =N(CH$_3$)$_2^+$; G is O, S, Se, SO$_2$, or C(CH$_3$)$_2$; each of J$^1$, J$^2$, J$^3$, and J$^2$, independently, is H, F, Cl, Br, or I; each of L$^1$ and L$^2$, independently, is H, —C(O)OH, or —SO$_3$H; and M$^1$ is —H, —CH$_3$, substituted amino, disubstituted amino, amido, —COOH, substituted or unsubstituted C$_{1-20}$ alkyl, substituted or unsubstituted C$_{2-20}$ heteroalkyl, or substituted or unsubstituted C$_{2-30}$ heterocyclyl.

Each R$^1$, R$^2$, R$^3$, R$^4$, R$^5$, or R$^6$ group can be substituted with one or more substituent groups. Substituted groups may have one, two, three or more substituents, which may be the same or different, each replacing a hydrogen atom. Substituents include halogen (e.g., F, Cl, Br, and I), hydroxyl, protected hydroxyl, amino (e.g., alkyl amino, dialkyl amino, or trialkyl ammonium), protected amino, carboxy, protected carboxy, cyano, methylsulfonylamino, alkoxy, acyloxy, nitro, sulfhydryl, phosphate, aryl groups, and lower haloalkyl. The substituent can also be a polymer, such as a functionalized polystyrene connected by a linking group to the photolabile protecting group.

An amino acid group is a moiety having an amino group and a carboxylic acid group, such as an α-amino acid. An amino acid includes the 20 common α-amino acids (Gly, Ala, Val, Leu, Ile, Ser, Thr, Asp, Asn, Lys, Glu, Gln, Arg, His, Phe, Cys, Trp, Tyr, Met and Pro), and other amino acids that are natural products, such as norleucine, ethylglycine, ornithine, gamma-amino butyric acid, and phenylglycine. A peptide group is composed of two or more amino acid groups linked by an amide bond.

A radical is a group of atoms that is bonded to moiety via a single bond through a single atom of the group. A diradical is a group of atoms that is bonded to moiety via two single bonds through two different atoms of the group.

An alkyl group is a branched or unbranched hydrocarbon that may be substituted or unsubstituted. Examples of branched alkyl groups include isopropyl, sec-butyl, isobutyl, tert-butyl, sec-pentyl, isopentyl, tert-pentyl, isohexyl. An alkenyl group contains one or more carbon-carbon double bonds. An alkynyl group contains one or more carbon-carbon triple bonds. Examples of cycloalkyl groups include cyclopropyl, cyclobutyl, cyclopentyl, cyclohexyl, cycloheptyl, and cyclooctyl. An aryl group is an aromatic ring, where the ring is made of carbon atoms. A cycloalkenyl group is a cycloalkyl containing a carbon-carbon double bond. A cyclitol radical is a cycloalkyl group having one or more hydroxyl groups (e.g., inositol).

An alkoxy group is an alkyl group linked to an oxygen atom through which it is linked to another moiety. When the leaving group is an alkoxy group, the alkoxide anion can be the conjugate base of an alcohol having a low pH. Examples of suitable alkoxy groups include —OCCl$_3$, and —OCF$_3$. An aryloxy group is an aryl group linked to an oxygen atom through which it is linked to another moiety. A thioalkoxy is an alkyl group linked to a sulfur atom through which it is linked to another moiety. An alkylsulfonyl or arylsulfonyl group is an alkyl or aryl group linked to a sulfonyl group through which it is linked to another moiety.

A heteroalkyl, a heteroalkenyl, heterocyclyl group contains at least one ring structure which contains carbon atoms and at least one heteroatom (e.g., N, O, S, or P). A heteroaryl is an aromatic heterocyclic radical. Examples of heterocyclyl radicals and heteroaryl groups include: thiazolyl, thienyl, furyl, 1-isobenzofuranyl, 2H-chromen-3-yl, 2H-pyrrolyl, N-pyrrolyl, imidazolyl, pyrazolyl, isothiazolyl, isooxazolyl, pyridyl, pyrazinyl, pyrimidinyl, pyradazinyl, indolizinyl, isoindolyl, indolyl, indazolyl, purinyl, phthalazinyl, cinnolinyl, benzoxazol-2-yl, benzothiazol-2- yl, or benzimidazol-2-yl, and pteridinyl. A heterocyclyl group may be attached to another moiety via a carbon atom or a heteroatom of the heterocyclic radical.

A saccharide group is a radical of a saccharide. A saccharide is a compound having the general formula $(CH_2O)_n$, including hexoses (n=6) and pentoses (n=5). A saccharide phosphate group is a saccharide radical bonded to at least one phosphate group. A polysaccharide group is a polymer composed of two or more saccharide groups bonded to each other. A lipid group is a radical derived from a lipid, which is composed of three fatty acid chains linked to a glycerol backbone by ester linkages. A nucleoside group is a radical including a base (e.g., a purine or a pyrimidine) linked to a saccharide group or a deoxy-saccharide group (e.g., ribose or deoxyribose, respectively). A nucleotide group is a nucleoside group linked to one or more phosphate moiety. A nucleoside monophosphate group is a nucleotide having a single phosphate moiety. A nucleoside diphosphate group is a nucleotide having a two phosphate moieties. A nucleoside triphosphate group is a nucleotide having a three phosphate moieties. A nucleoside thiophosphate group is a nucleotide in which at least one oxygen atom of a phosphate group is replaced by a sulfur atom. A polynucleotide group is a polymer composed of two or more nucleotide groups bonded to each other.

The caging group can interfere with the binding, reactivity, or activity of the compound. For example, caged amino acids can be used in the automated synthesis of peptides that may be biologically inactive until photolyzed. Amino acids caged on the α-amine can block the N-terminus of the peptide during synthesis.

In another example, caged compounds can also be used to probe the effects of the uncaged compounds in a biological sample. Biological samples can include muscle fibers, muscle cells, brain tissue, brain cells, fibroblasts, sarcoplasmic reticulum vesicles, submitochondrial particles, membrane fragments, samples containing regulatory proteins. In addition, caged chelants can bind metal ions, for example, $Ca^{2+}$ or $Mg^{2+}$. The affinity of the chelant for a particular metal ion can change when the protecting group is removed by photolysis. This change in affinity can lead to a rapid and localized change (e.g., increase or decrease) in metal ion concentration, which can permit changes in localized metal ion concentration changes to be studied.

The halogenated coumarin- and xanthene-based caging groups attached to the leaving group via a —$CHM^1$-group (e.g., a $CH_2$ group) to a site that undergoes a large increase in electron density upon excitation of the delocalized chromophore. The halogen atoms of the coumarin-based group and the extended conjugation of the xanthene based group are added to promote intersystem crossing to the triplet state. These design principles can be applied to other fluorescent dyes to create other caging groups of longer wavelengths and larger one photon and two photon cross-sections. For use in one photon photolysis, longer wavelengths and greater photosensitivity can help minimize photodamage, decrease irradiation times, simplify experimental apparatus, make semiconductor light sources feasible for uncaging, and permit separate and controllable photolyses of two or more protecting groups at different wavelengths.

The two-photon photolysis can use less energy and be less damaging to the surroundings of the compound being uncaged. A high degree of three-dimensional spatial precision can be obtained by excitation with two or more coincident infrared photons of equivalent total energy. Such multiphoton excitation can require extremely high local intensities, typically obtained by focusing a femtosecond pulsed infrared (IR) laser with a high-numerical-aperture lens, and becomes insignificant away from the point of focus. This nonlinear optical phenomenon can be used to noninvasively localize the photochemistry to any given spot in three dimensions and can be especially valuable in mapping biochemical sensitivities in complex tissues such as the brain. Photosensitivity is quantified as the uncaging action cross-section $\delta_u$, which is the product of the two-photon absorbance cross-section $\delta_a$ and the uncaging quantum yield $Q_{u2}$. Ideally, $\delta_u$ should exceed 0.1 GM, where GM or Goeppert-Mayer is defined as $10^{-50}$ $cm^4 \cdot s/photon$. Carboxylate, phosphate, and carbamate esters of brominated 6-hydroxycoumarin-4-ylmethanol have the requisite action cross-sections ($\delta_u \sim 1$ GM), photolysis kinetics, synthetic accessibility, water solubility, and stability in the dark to be used in the true two-photon uncaging of biologically important acids and amines. In addition, their cross-sections for one-photon uncaging with UV radiation at 365 nm or longer are high. Two-photon photolysis can lead to higher-resolution three-dimensional optical memories, spatially arrayed combinatorial libraries, photodynamic therapy, and deeper and less-invasive mapping of the local responses of complex tissues to neurotransmitters and messengers.

Other features or advantages of the present invention will be apparent from the following detailed description and from the claims.

DESCRIPTION OF THE PREFERRED EMBODIMENTS

Figure 1:
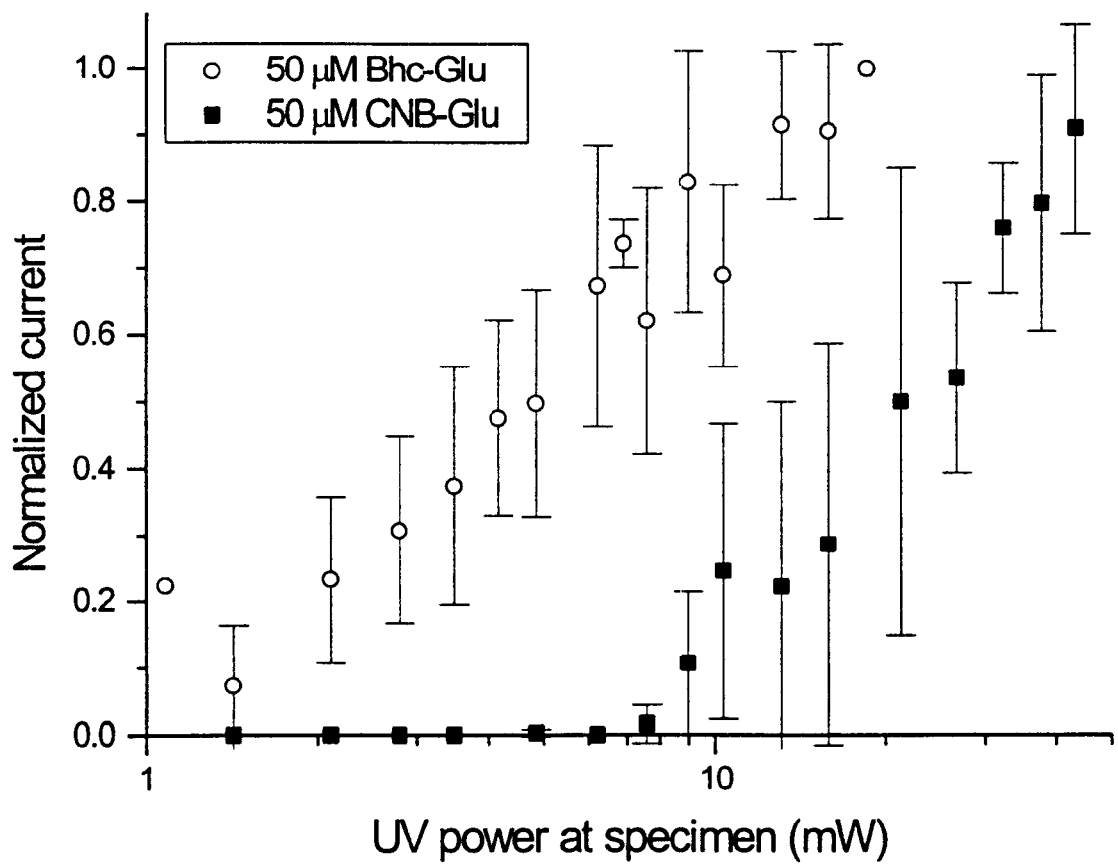
FIG. 1 is a graph depicting responses of rat cortical neurons to one-photon UV uncaging of caged glutamate compounds.

A photolabile protecting group which is a derivative of a halogenated coumarin or quinoline-2-one can be prepared by the following general condensation reaction shown in the following equation:

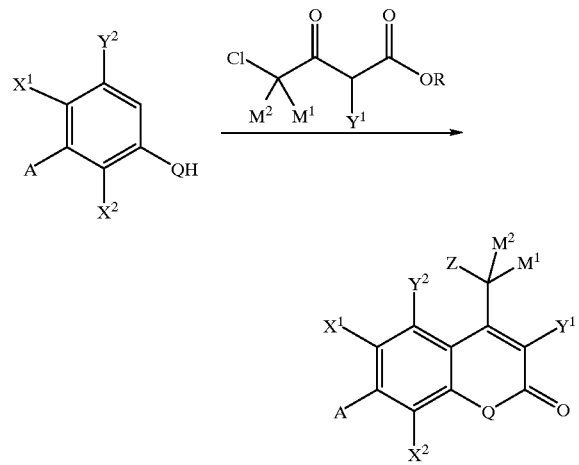

The substituents in the reaction are described above. It may be necessary to employ protecting groups generally known in the art to facilitate the depicted condensation reaction. More specifically, one photolabile protecting group can be a halogenated coumarin group prepared according to the following reaction:

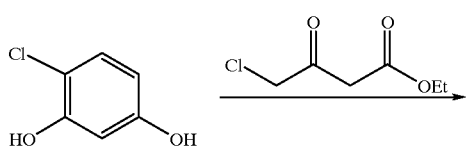

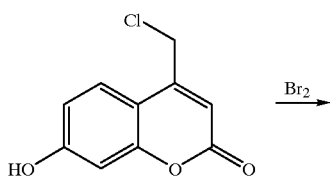

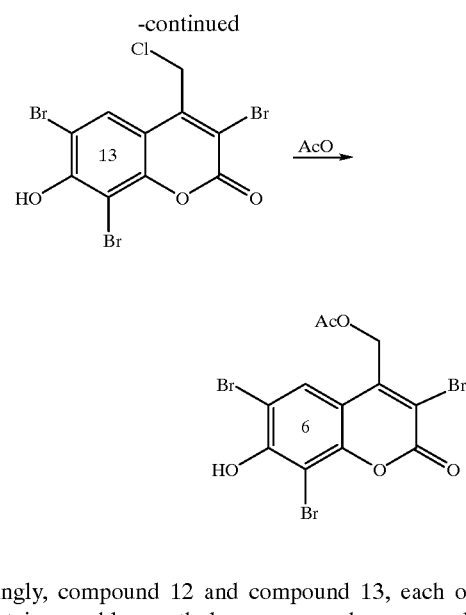

Alternatively, a coumarin-containing compound can be brominated, as shown in the following reaction:

Accordingly, compound 12 and compound 13, each of which contains a chloromethyl group, can be prepared. These compounds can be used to derivitize a number of compounds with the photolabile protecting group, as described below. As shown, compound 4 and compound 6 can be prepared by alkylation of a carboxylate group.

Another photolabile protecting group can be a quinoline-2-one group prepared according to Scheme A. Various quinoline-2-one derivatives can be prepared by the ring-forming and halogenation reactions shown in the scheme. Scheme A also illustrates a number of reaction pathways to form quinoline-2-one derivatives having leaving groups Z. Additional halogen groups can be placed on the quinolin-2-one rings by halogenation under more forcing conditions.

Scheme A

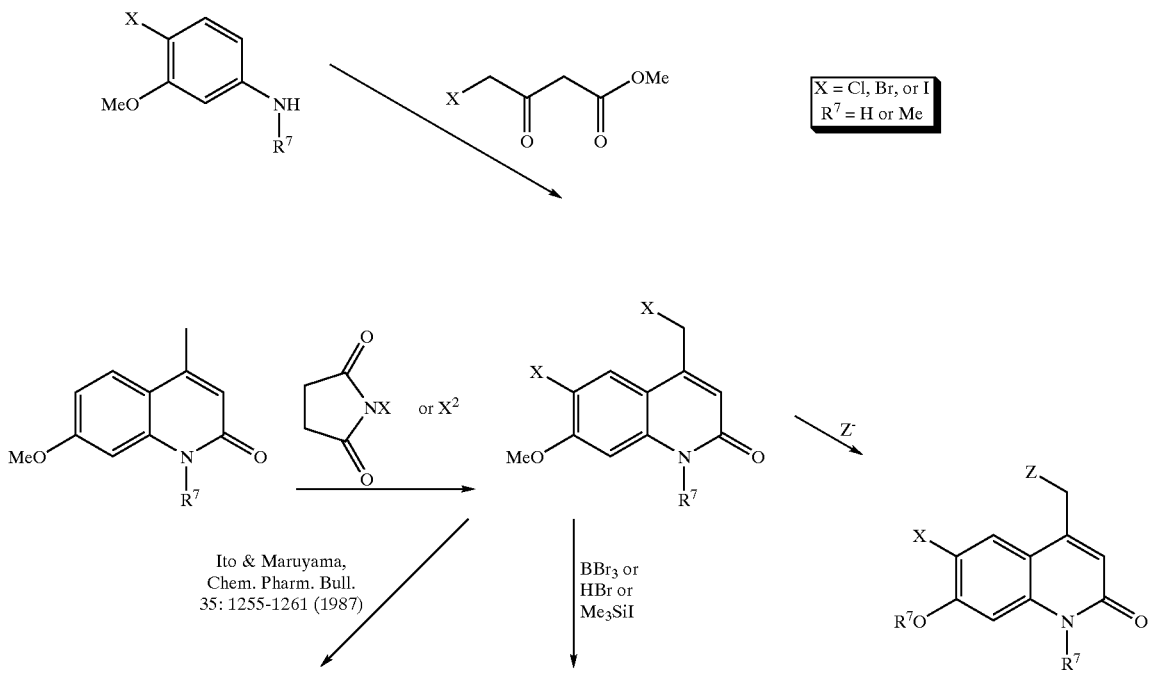

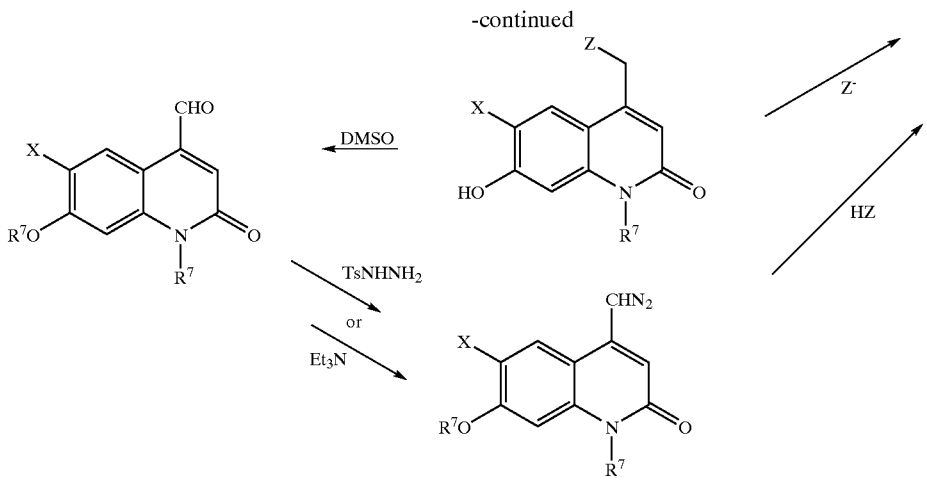

In another example, photolabile protecting groups can be prepared by the following general reactions shown in Scheme B. In Scheme B, the bis(hydroxyphenyl)G compounds

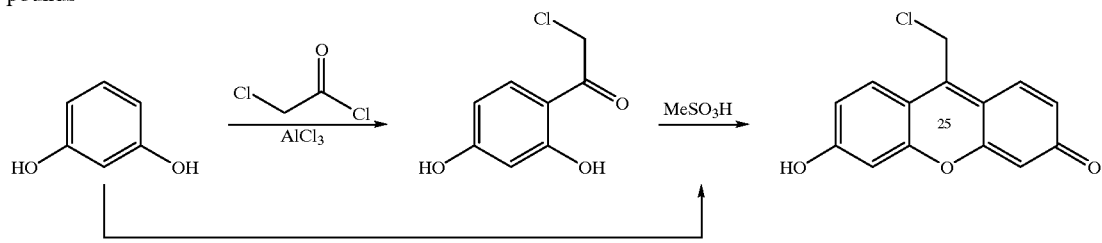

are described in Pfoertner, *J. Chem. Soc. Perkin* 2 523–526 (1991) (where G is S, SO$_2$, or Se) and von Braun, *Liebigs Ann.* 507:14–24 (1933) (where G is CMe$_2$). In addition to thioxanthene, selenoxanthene, anthracene derivatives, a xanthene derivative can be prepared by the following set of reactions:

Scheme B

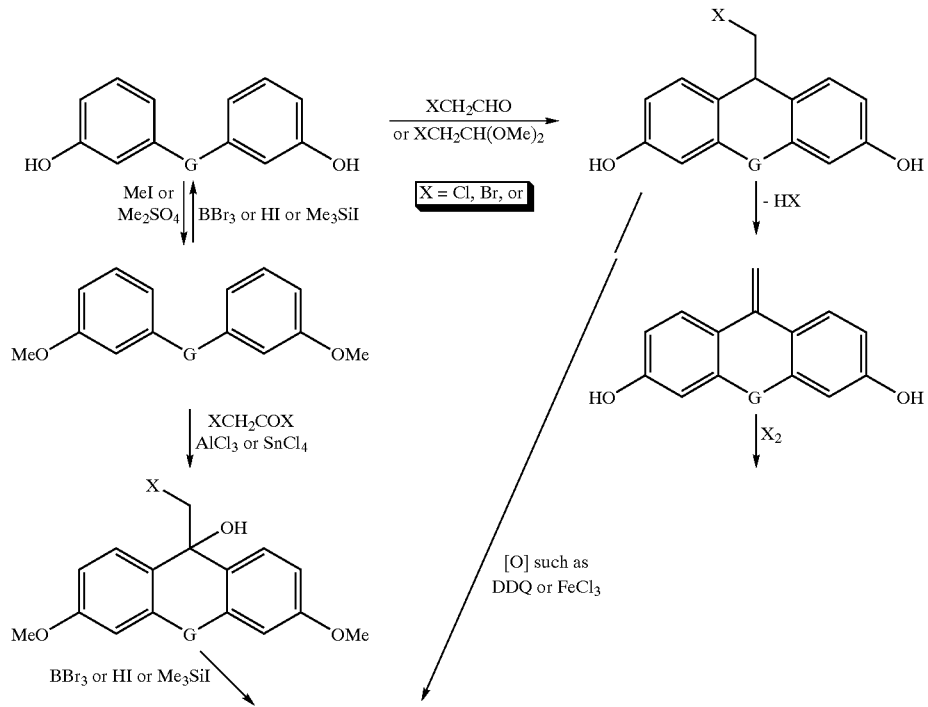

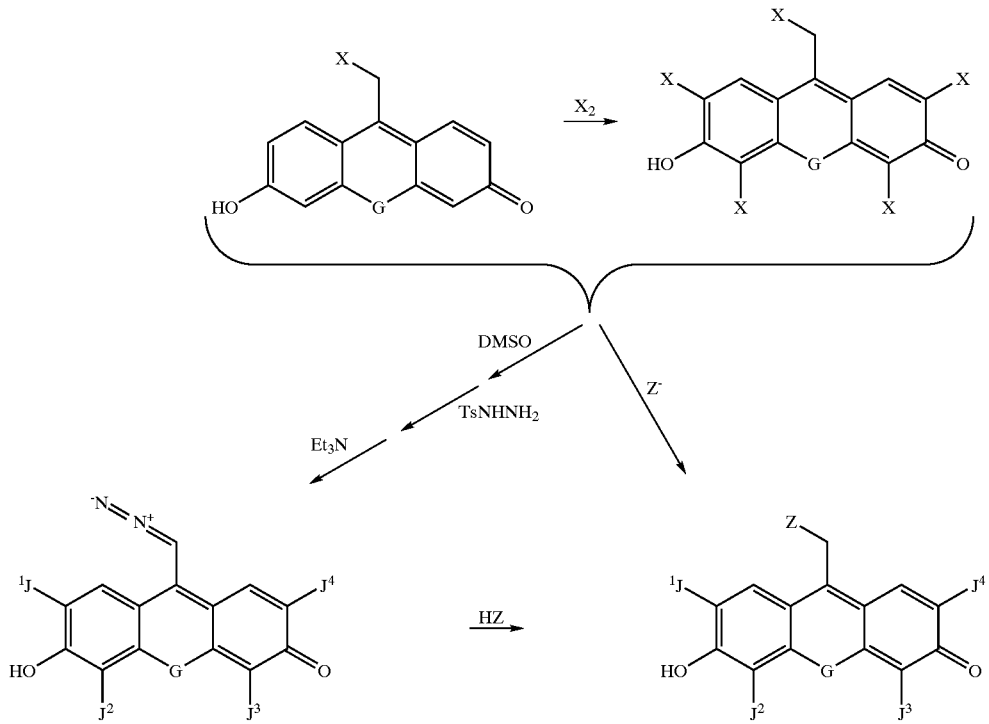

Generally, the photolabile protecting group can be linked to the compound to be caged as a leaving group (e.g., a conjugate base of a biologically active molecule) via an ether (e.g., an aryloxy group), thioether, ester (including phosphate ester), amine, carbonate, carbamate or similar linkage to a heteroatom (usually O, S or N). The following reactions, while illustrative for the halogenated coumarin-derived photolabile protecting groups, can be modified to employ other photolabile protecting groups. In the reactions described herein, HO—, $H_2N$—, or MeNH— groups can be masked temporarily using non-photolabile protecting groups. See, Greene, T. W. and Wuts, P. G. M., *Protective Groups in Organic Synthesis*, 2nd ed., Wiley, New York (1991).

In one example of a caging reaction, a wide range of compounds containing an at least weakly acidic group, such as a carboxylic acid group, a sulfonic acid group, a phosphoric acid group, a phosphonic acid group, a thiol group, a phenol group, or an amine group, can be caged by the reaction of a halogenated coumarinylmethyl halide derivative in the presence of the compound to be caged (Z-H), in the presence of a H-halogen scavenger, such as triethylamine, diisopropylethylamine, 1,8-diazabicyclo [5.4.0]undec-7-ene (DBU), NaH, or $Ag_2O$, as depicted in the following equation:

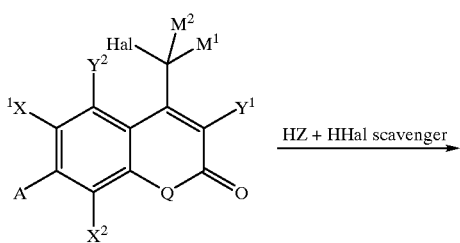

In another example, compounds of the formula Z-H (e.g., carboxylic acid, sulfonic acid, phosphoric acid, or phosponic acid groups, or a hydrogen halide) can be caged with a diazomethane derivative of the photolabile protecting group, as depicted in the following equation:

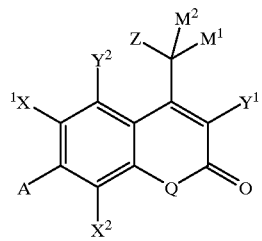

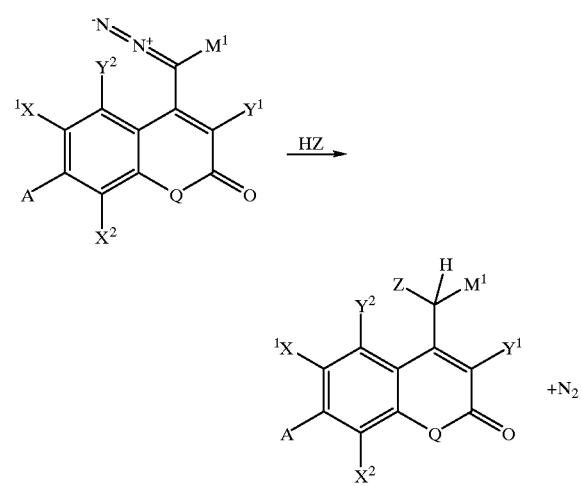

In another example, compounds of the formula Z-OH or Z-NHR can be caged as carbonate or carbamate derivatives of the photolabile protecting group. An activated carbonate intermediate can be prepared which further reacts with the Z-OH or Z-NHR group to form the caged compound, as depicted in the following equations:

Generally, uncaging can be accomplished rapidly (e.g., in microseconds to milliseconds) with irradiation, for example, using a laser, a semiconductor photodiode, or a flashlamp. The efficiency and wavelength required for uncaging can depend on the structure of the caging group and the atom to which it is attached.

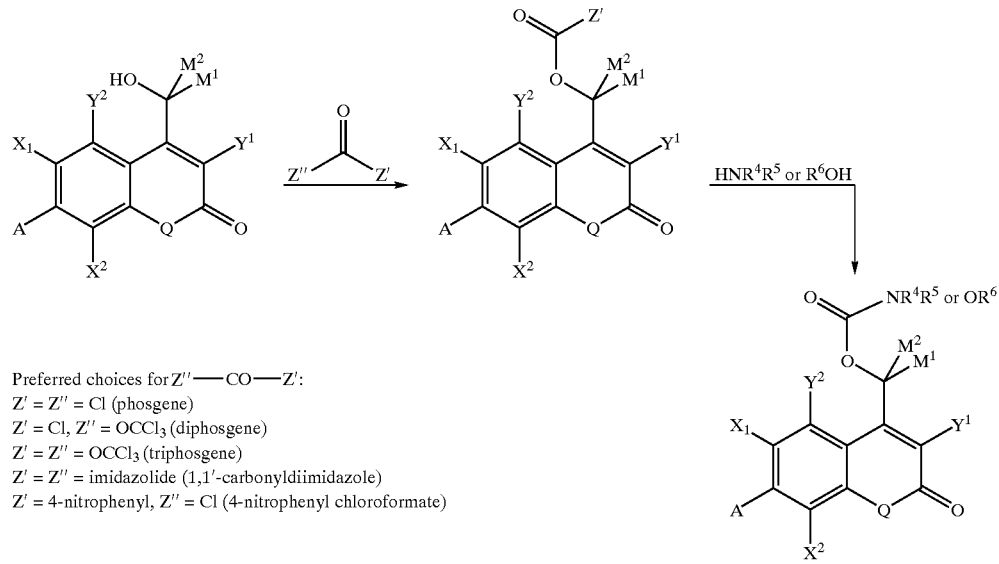

Preferred choices for Z''—CO—Z':
Z' = Z'' = Cl (phosgene)
Z' = Cl, Z'' = OCCl$_3$ (diphosgene)
Z' = Z'' = OCCl$_3$ (triphosgene)
Z' = Z'' = imidazolide (1,1'-carbonyldiimidazole)
Z' = 4-nitrophenyl, Z'' = Cl (4-nitrophenyl chloroformate)

The photolabile protecting groups of the invention can be removed from a compound when the caging group is bonded to a leaving group portion of the compound. Photolysis of the photolabile protecting group with radiation of the appropriate wavelength generates an excited state of the protecting group which then undergoes hydrolysis, uncaging the compound. For example, uncaging of the compound carbamate and carbonate groups can occur by a two-step process, first yielding a carbamic acid or carbonic acid derivative, respectively, which spontaneously decarboxylates to yield the compound. An example of the uncaging reaction of a photolabile protecting group bonded to a leaving group Z to release the compound Z-H is depicted in the following equation:

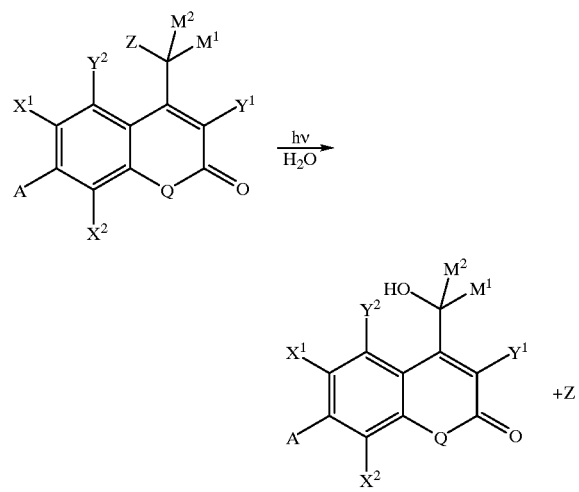

The photolabile protecting groups can be used to protect a wide variety of compounds. Compounds that can be readily caged and uncaged by the protecting groups include nucleotides (e.g., ATP, ADP, cAMP, GTP, GDP, GTP-γ-S, GDP-β-S, cGMP, 8-substituted derivatives of cAMP or cGMP, such as 8-bromo-cAMP or cGMP, 8-chloro-cAMP or cGMP and 8-parachlorophenylthio (cCPT) cAMP or cGMP), phosphates (e.g., phosphate and phosphate esters), chelants (e.g., EDTA, EGTA), ionophores (e.g., nigericin), NO (e.g., generated from the decomposable compound HON=N(O) (NEt$_2$)), nucleosides, nucleoside derivatives, nucleotide derivatives (e.g., cADP-ribose, 8-amino-cADP-ribose, or 8-bromo-cADP-ribose), cyclitols (e.g., inositol) and cyclitol phosphates (e.g., a myo-inositol phosphate, myo-inositol-1,4,5-triphosphate, myo-inositol-1,3,4,5-tetrakisphosphate, or myo-inositol-3,4,5,6-tetrakisphosphate), luciferin, enzyme inhibitors, fatty acids (e.g., arachidonic acid), protein kinase C activators (e.g., dioctanoylglycerol), tubulin assembly promoters (e.g., paclitaxel), a tubulin-assembly promoter, antibiotics (e.g., penicillins or A23187), neurotransmitters (e.g., L-glutamic acid, aspartic acid, carbamylcholine, dopamine, epinephrine, GABA, glutamic acid, glycine, haloperidol, isoproterenol, kainic acid, NMDA, NMDA receptor antagonist MK-801, norepinephrine, phenylephrine, propranolol, or serotonin), and fluorescent dyes (e.g., fluorescein, HPTS, rhodamines, succinimidyl esters and sulfosuccinimidyl esters of carboxy-Q-rhodamine, or Rhodamine Green). The compound can be cell permeant, as described, for example, in Furuta, et al., Biochem. Biophys. Res. Commun., 228:193–198 (1996).

Examples of compounds including the photolabile protecting groups (Pg-CHM$^1$-) include:

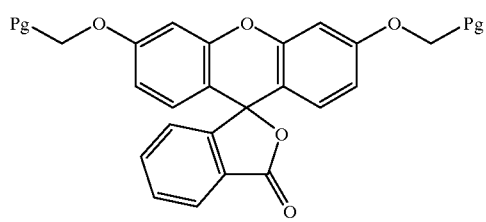

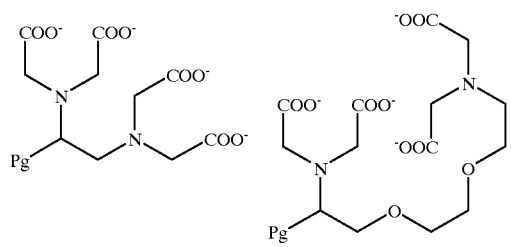

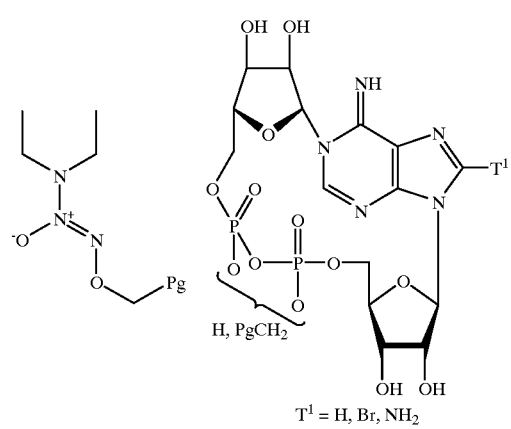

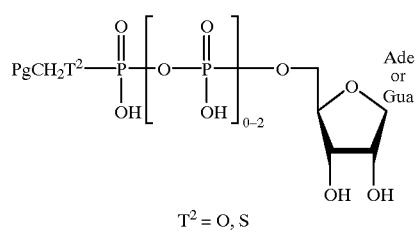

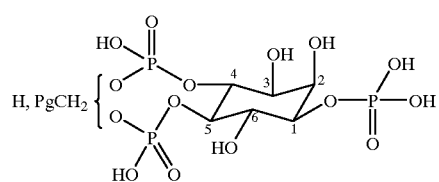

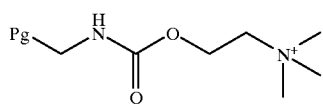

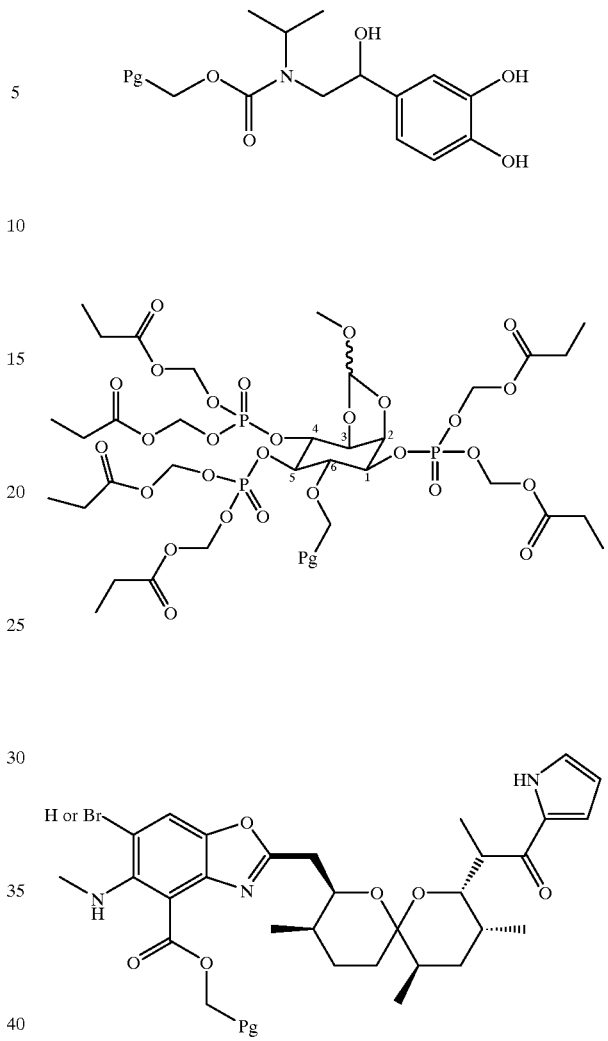

Scheme I depicts exemplary synthetic routes to various halogenated coumarin derivatives, including a chloromethyl derivative compound 11, an acetoxymethyl derivative compound 5, a hydroxymethyl derivative compound 14, and ester, carbamate, and carbonate derivatives such as protected glutamate derivatives compound 16 and compound 15, and caged gamma-glutamate derivatives compound 8 and compound 7. The scheme illustrates methods that can be used to prepare physiologically useful caged compounds by linking a 6-bromo-7-hydroxycoumarin-4-ylmethyl group to a carboxylate or an amine (e.g., of an amino acid) via a carbamate or ester linkage.

Scheme II depicts an exemplary synthetic routes to various halogenated coumarin derivatives via a diazomethyl derivative of a halogenated coumarin derivative. According to the reactions depicted in Scheme II, the 6-bromo-7-hydroxycoumarin-4-ylmethyl group can cage phosphate esters such as a diethyl phosphate (compound 23) or a cyclic adenosine-3',5'-monophosphate (cAMP) (compound 24). The intermediate diazomethyl derivative (compound 21) was prepared by treatment of the tosylhydrazone (compound 20) with a base.

Scheme I
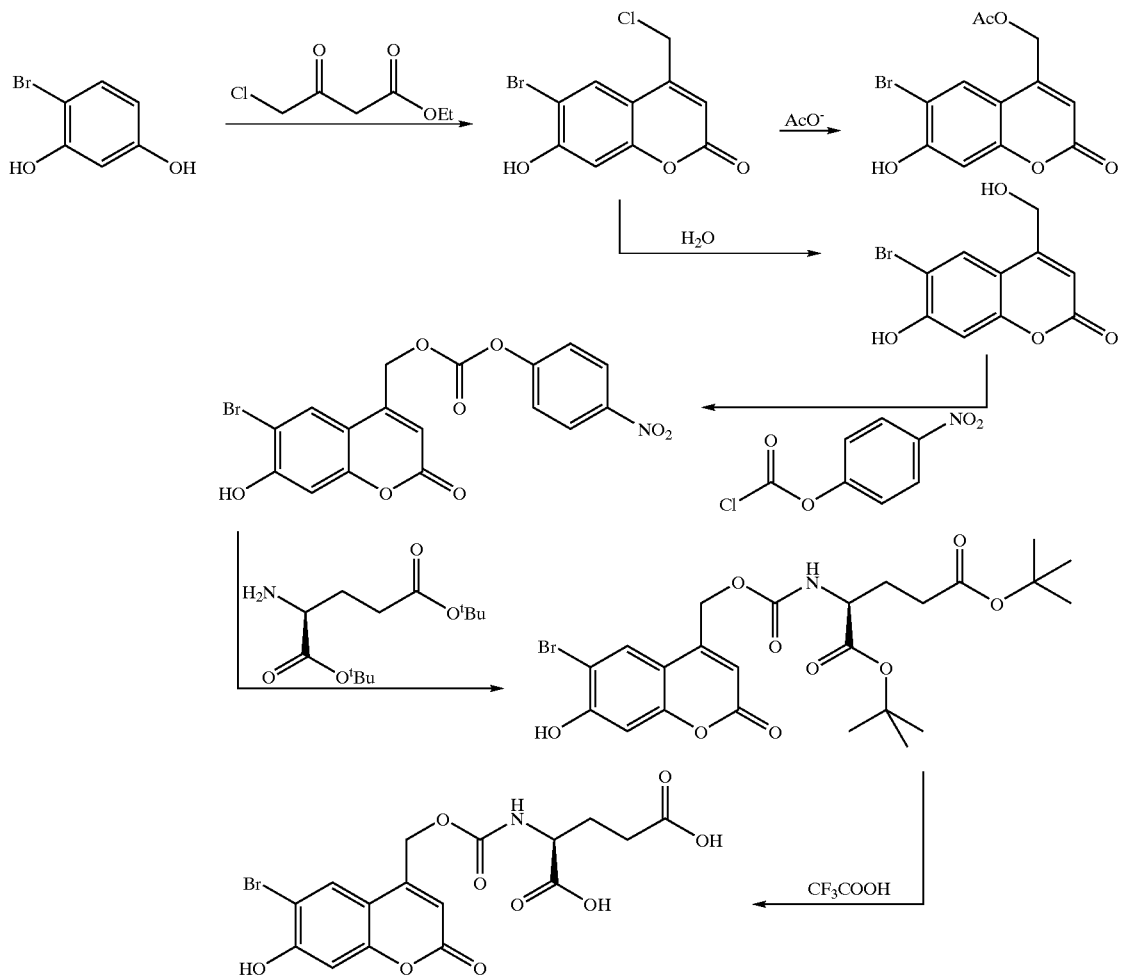
Scheme II
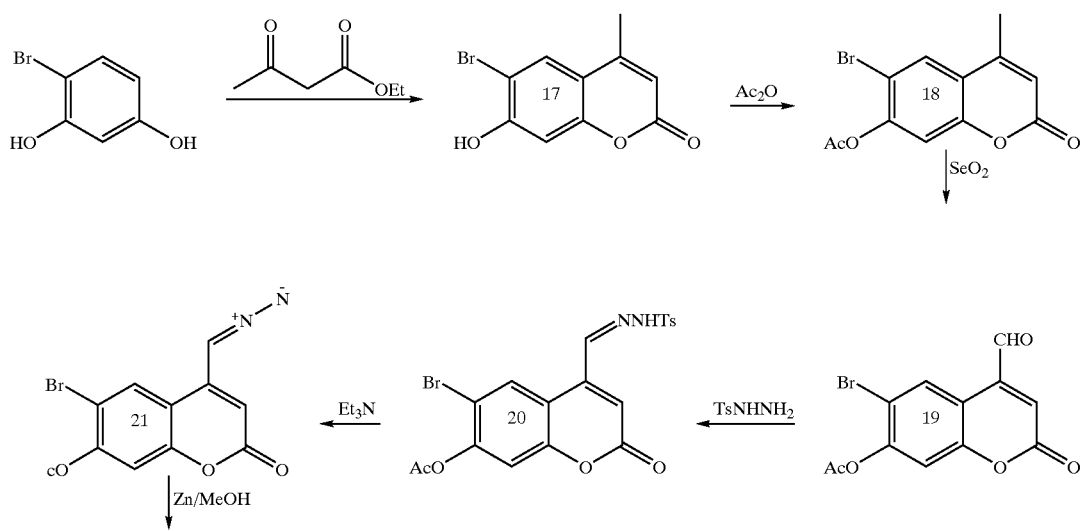

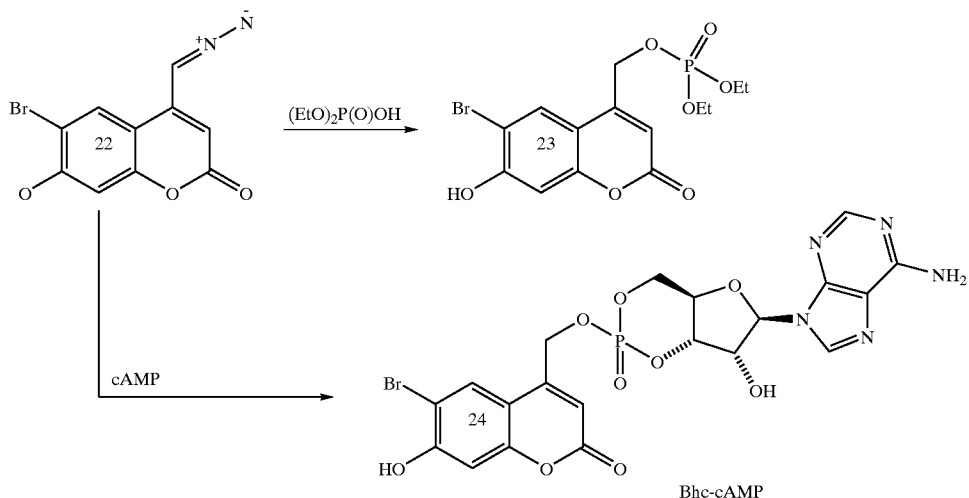

Scheme III depicts routes to the synthesis of caged ethylene diamine tetraacetic acid (EDTA) derivatives, adapted from similar syntheses described by Ellis-Davies, G. C. R. and Kaplan, J. H., *J. Org. Chem.*, 53:1966–1969 (1988). The caging group is a brominated hydroxy coumarin. The degree of bromination of the coumarin group can depend on the bromination conditions, with more bromination occurring under more forcing conditions (e.g., higher bromine concentration and/or higher temperature). One route involves alkylation of an amine, $HN(CH_2CO_2Me)_2$. The other route involves formation of a coumarin BIS(azide) compound, followed by its reduction and subsequent alkylation.

Scheme IV depicts two routes to the synthesis of caged ene glycol BIS(ethylene amine) tetraacetic acid (EGTA) derivatives, adapted from a similar synthesis described by Ellis-Davies, G. C. R. and Kaplan, J. H., *Proc. Nat. Acad. Sci.*, 91:187–191 (1994). The routes employ different methoxy coumarin compounds. The caging group is a brominated hydroxy coumarin. The reaction conditions can be altered to allow other coumarin derivatives (e.g., methoxy or acyloxy coumarin derivatives) to be prepared.

Scheme III

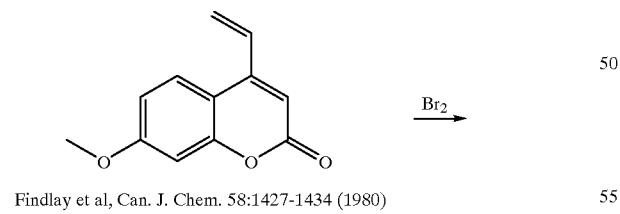

Findlay et al, Can. J. Chem. 58:1427-1434 (1980)

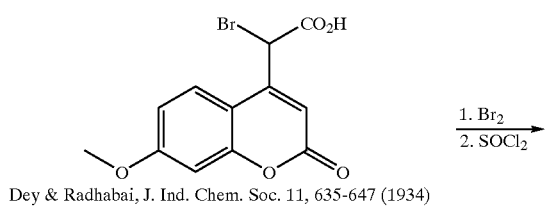

Dey & Radhabai, J. Ind. Chem. Soc. 11, 635-647 (1934)

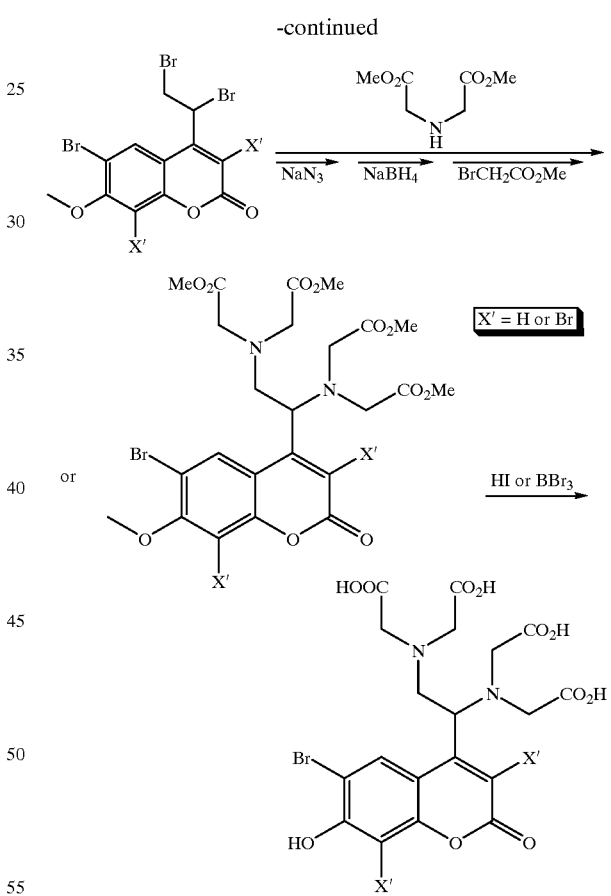

Scheme IV

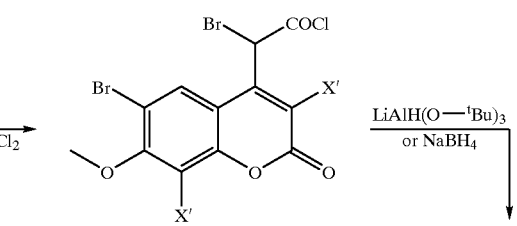

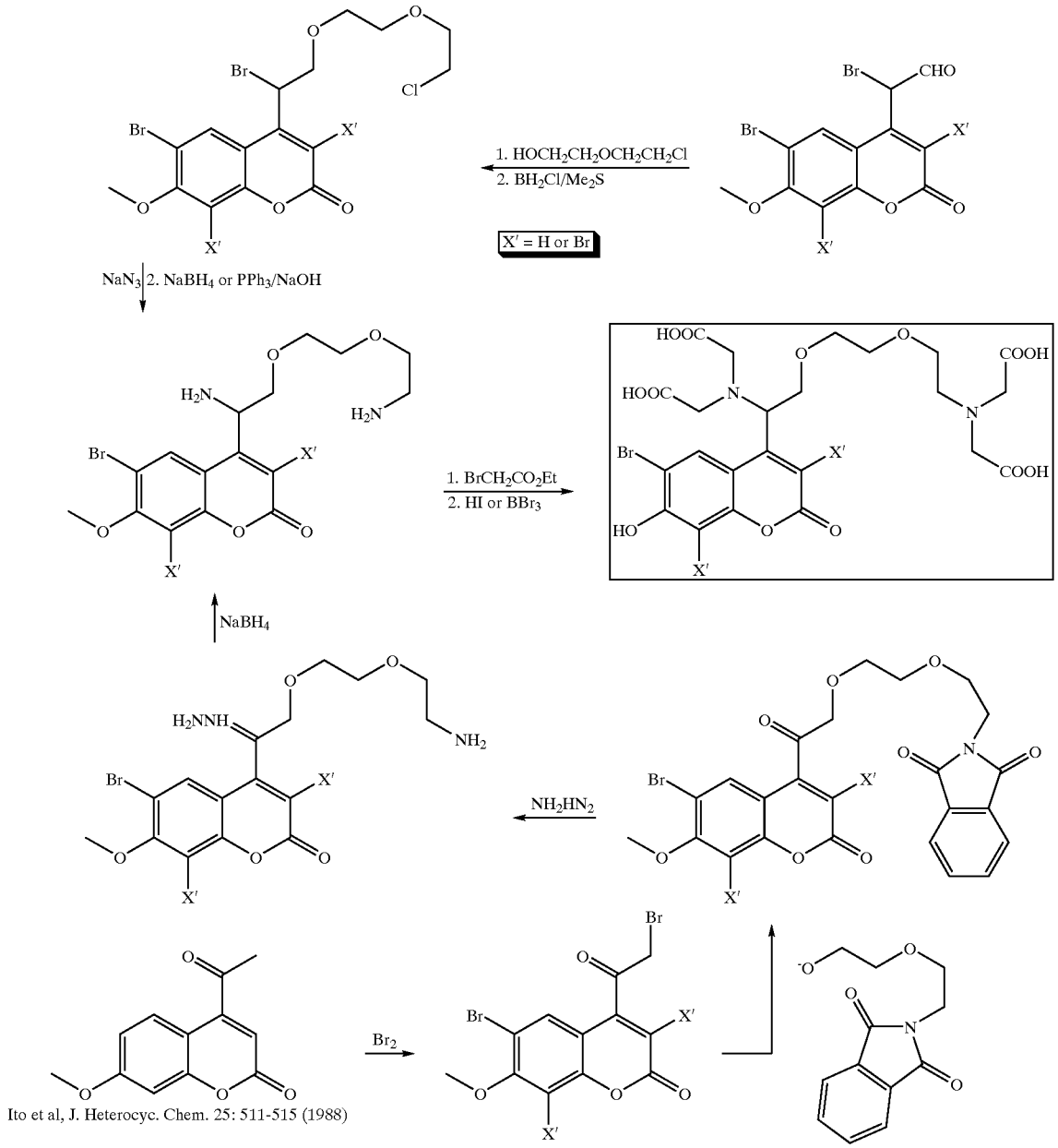

Ito et al, J. Heterocyc. Chem. 25: 511–515 (1988)

Photolabile linker groups can also be prepared using the photolabile protecting groups. The photolabile linker can be released from the group Z by photolysis. The linker groups can provide a connection to, for example, a polymer surface (e.g., polymer beads) or an affinity tag. The polymer can be a functionalized polymer such as, for example, a functionalized polyethylene glycol or a functionalized polystyrene.

For example, Olejnik, et al., *Methods Enzymol.* 291:135–154 (1998) describes the use of affinity tags for the isolation and detection of biomolecules and Marriott and Ottl, et al., *Methods Enzymol.* 291:155–175 (1998) describes cross-linking agents. In these example, $M^1$ can be a substituted or unsubstituted alkyl, heteroalkyl, or heterocyclyl group, or A can be a substituted or unsubstituted alkoxy group. Examples of photocleavable linking group-containing linking groups are as follows:

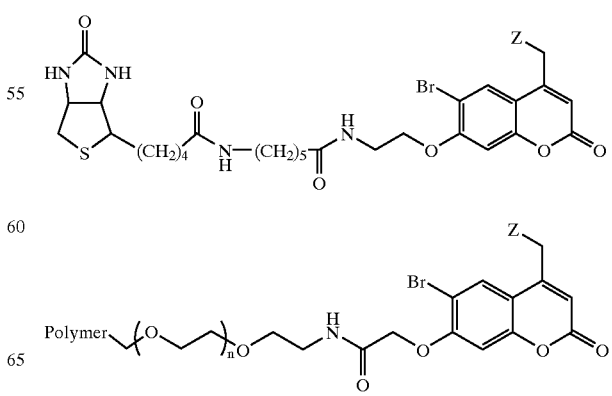

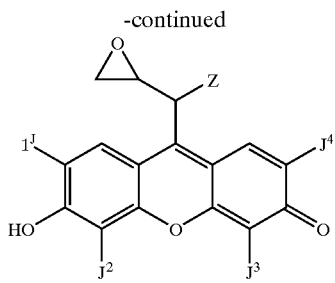

A compound that differs from a compound specifically disclosed herein by having one or more non-photolabile protecting groups is within the invention. For example, where a compound differs from a compound disclosed herein only in that one or more hydrogens from a thiol-, amino-, or hydroxyl-moiety (or a hydrogen or hydroxyl from a carboxyl moiety) has been substituted with a non-photolabile protecting group to form a carboxyl or sulfonyl ester or amide, that compound is within the invention. Sulfonyl esters include alkylsulfonyls (e.g., methylsulfonyl or mesyl) and arylsulfonyls (e.g., tosyl). Further examples and conditions are found in T. W. Greene, *Protective Groups in Organic Chemistry*, (1st ed., 1981; 2nd ed., 1991, T. W. Greene and P. G. M. Wuts).

Without further elaboration, it is believed that one skilled in the art can, based on the description herein, utilize the present invention to its fullest extent. The following examples are, therefore, to be construed as merely representative, and not limitive, of the remainder of the disclosure. All publications cited in this disclosure are incorporated by reference.

EXAMPLE 1

Synthesis

Generally, chemicals and solvents were used directly as received unless otherwise noted. Acetonitrile, chloroform and dichloromethane were dried over 4A molecular sieves. Proton magnetic resonance spectra ($^1$H NMR) were recorded on a Gemini 200 MHz spectrometer (Varian; Palo Alto, Calif.) and reported in ppm (δ) downfield from tetramethylsilane with residual solvent peaks as the internal standards. Ultraviolet spectra were recorded on a Cary 3E UV-Visible spectrophotometer (Varian, Palo Alto, Calif., USA). Fluorescence spectra were recorded on a Fluorolog spectrofluorometer (SPEX; Edison, N.J., USA). Mass spectra were recorded on a electrospray mass spectrometer (5989B, Hewlett-Packard; Palo Alto, Calif., USA). Thin layer chromatography (TLC) and column chromatography were performed on precoated silica gel 60F-254 plates and 230–400 mesh silica gel 60 respectively (EM Separations; Gibbstown, N.J., USA). All manipulations of compounds sensitive to near ultraviolet light were performed under an orange safety lamp.

6-Bromo-4-chloromethyl-7-hydroxycoumarin (11).

A solution of 936.1 mg (4.953 mmol) 4-bromoresorcinol, concentrated sulfuric acid (5 mL) and ethyl 4-chloroacetoacetate (1 mL, 7.4 mmol) was stirred for 6 days at room temperature. The reaction mixture was poured into ice-water and stirred for 2 hours to give a fine precipitate. The precipitate was collected by filtration, washed with cold water and dried under vacuum over $P_2O_5$ to yield 847.6 mg (2.928 mmol, 59.1% yield) of compound 11 as a solid. $^1$H NMR ($CD_3OD$) δ 7.96 (1H, s), 6.86 (1H, s), 6.43 (1H, s), 4.83 (2H, s).

6-Bromo-7-hydroxycoumarin-4-ylmethyl acetate (5).

A mixture of 67.1 mg (0.232 mmol) of compound 11, dry benzene (2 mL), 175 mL (0.927 mmol) of 1,8-diazabicyclo[5.4.0]undec-7-ene, and 40 mL (0.70 mmol) of acetic acid was refluxed for 1.5 hours. The reaction mixture was allowed to cool to room temperature, diluted with chloroform (10 mL), quenched with 1N HCl (1 mL) and separated. The organic layer was dried over $MgSO_4$ and evaporated to yield the crude product. Purification by column chromatography (10 g of $SiO_2$, 4.7% methanol-chloroform) gave 43.1 mg (0.138 mmol, 59.4% yield) of compound 5 as an oil. $^1$H NMR ($CDCl_3$+5% $CD_3OD$) δ 7.56 (1H, s), 6.80 (1H, s), 6.21 (1H, s), 5.14 (2H, s), 2.11 (3H, s); MS (ES, negative) 311.0 and 313.1; UV (KMOPS, pH 7.2) λmax (ε) 370 nm (15,000 $M^{-1}cm^{-1}$).

6-Chloro-4-chloromethyl-7-hydroxycoumarin (12).

This compound was prepared by the same method as compound 11, starting with 4-chlororesorcinol rather than 4-bromoresorcinol, to yield 2.50 g (99% yield) of compound 12 as a solid. $^1$H NMR ($CD_3OD$) δ 7.96 (1H, s), 6.86 (1H, s), 6.43 (1H, s), 4.83 (2H, s).

6-Chloro-7-hydroxycoumarin-4-ylmethyl acetate (4).

This compound was prepared by the same method as compound 5, starting with compound 12 rather than compound 11, to yield 75.4 mg (0.281 mmol, 28% yield) of compound 4 as an oil. $^1$H NMR ($CDCl_3$+5% $CD_3OD$) δ 7.43 (1H, s), 6.85 (1H, s), 6.25 (1H, s), 5.16 (2H, s), 3.30 (1H, s), 2.14 (3H, s); MS (ES, negative) 267.2 and 269.1; UV (KMOPS, pH 7.2) λmax (ε) 370 nm (16,000 $M^{-1}cm^{-1}$). ps 3,6,8-Tribromo-4-chloromethyl-7-hydroxycoumarin (13).

To a suspension of 212.6 mg (1.01 mmol) of 4-chloromethyl-7-hydroxycoumarin in acetic acid (2 mL) was added 0.2 mL (3.9 mmol) of bromine. The mixture first became a brown solution and then a yellow-orange slurry. After 1 hour at room temperature, the reaction mixture was poured into ice-water (70 mL) and allowed to stand at room temperature for 2 hours. The yellow precipitate was collected by filtration, washed thoroughly with cold water and dried over $P_2O_5$ under vacuum to give 477.2 mg of crude 13 as an orange solid. This compound was used for the next reaction without further purification. $^1$H NMR ($CD_3OD$) δ 8.14 (1H, s), 4.83 (2H, s).

3,6,8-Tribromo-7-hydroxycoumarin-4-ylmethyl acetate (6).

This compound was prepared by the same method as compound 4, starting with compound 13 rather than compound 12, to yield 34.5 mg (73.3 mmol, 30% yield) of compound 6 as an oil. $^1$H NMR ($CDCl_3$+5% $CD_3OD$) δ 7.88 (1H, s), 5.42 (2H, s), 2.11 (3H, s); MS (ES, negative) 466.9, 468.9, 470.9 and 472.9; UV (KMOPS, pH 7.2) λmax (ε) 397 nm (15,900 $M^{-1}cm^{-1}$).

6-Bromo-7-hydroxy-4-hydroxymethylcoumarin (14).

A suspension of 291.7 mg (1.008 mmol) of compound 11 in water (50 mL) was refluxed for 14 hours. The resulting solution was cooled and evaporated to give 268.7 mg (0.9913 mmol, 98% yield) of compound 14 as a solid, pure enough to use in the next step without further purification. $^1$H NMR ($CD_3OD$) δ 7.83 (1H, s), 6.86 (1H, s), 6.40 (1H, s), 4.78 (2H, s).

Di-tert-butyl-N-(6-bromo-7-hydroxycoumarin-4-yl) methoxycarbonyl glutamate (15).

To a stirred solution of 61.1 mg (0.225 mmol) of alcohol 14 in dry acetonitrile (5 mL) were added 56.9 mg (0.466 mmol) of 4-dimethylaminopyridine and 52.3 mg (0.252 mmol) of 4-nitrophenyl chloroformate simultaneously, to generate an intermediate mixed carbonate. After stirring for 7 hours at room temperature, another 58.1 mg (0.476 mmol) of 4-dimethylaminopyridine and 73.2 mg (0.247 mmol) of di-tert-butyl glutamate hydrochloric acid salt were added. The reaction mixture was stirred at room temperature for 23 hours, quenched with 15% citric acid, diluted with chloroform and separated. The organic layer was dried ($MgSO_4$) and evaporated to dryness to yield the crude product. Purification by column chromatography (15 g of $SiO_2$, 33% ethyl acetate-hexane then 60% ethyl acetate-hexane) gave 47.0 mg (0.0845 mmol, 37.5% yield) of compound 15 as an oil and 29.0 mg (0.107 mmol, 47.5% recovery) of the recovered alcohol 14. Compound 15 had $^1$H NMR ($CDCl_3$) δ 7.63 (1H, s), 7.01 (1H, s), 6.36 (1H, s), 5.67 (1H, d, J=8 Hz), 5.22 (2H, s), 4.28 (1H, m), 2.3–2.4 (2H, m), 2.15 (1H, m), 1.95 (1H, m), 1.48 (9H, s), 1.45 (9H, s); MS (ES, negative) 553.9 and 555.9.

N-(6-Bromo-7-hydroxycoumarin-4-yl)methoxycarbonyl glutamate (7).

A solution of 16.9 mg (0.0304 mmol) of 15 in dry dichloromethane (3 mL) and trifluoroacetic acid (1 mL) was stirred for 2 days at room temperature and evaporated to dryness. Purification by column chromatography (8 g of $SiO_2$, 25% methanol-chloroform containing 0.4% acetic acid) gave 12.7 mg (0.0286 mmol, 94.1% yield) of compound 7 as a yellow solid. $^1$H NMR ($D_2O$) δ 7.72 (1H, s), 6.80 (1H, s), 6.26 (1H, s), 5.17 (2H, s), 3.96 (1H, m), 2.3–2.4 (2H, m), 2.10 (1H, m), 1.90 (1H, m); MS (ES, positive) 466.1 and 468.2 (M+$Na^+$), 482.1 and 483.9 (M+$K^+$); UV (KMOPS, pH 7.2) λmax (ε) 368 nm (17,470 $M^{-1}cm^{-1}$).

N-(tert-Butoxycarbonyl)-α-tert-butyl-γ-(6-bromo-7-hydroxycoumarin-4-yl)methyl glutamate (16).

A mixture of 56.0 mg (0.193 mmol) of 6-bromo-4-chloromethyl-7-hydroxycoumarin (compound 11), dry benzene (3 mL), 83 mL (0.44 mmol) of 1,8-diazabicyclo[5.4.0]undec-7-ene and 66.4 mg (0.219 mmol) of N-(tert-butoxycarbonyl)-α-tert-butyl glutamate was refluxed for 1 hour. The reaction mixture was allowed to cool to room temperature, diluted with chloroform, quenched with 15% citric acid and separated. The organic layer was dried ($MgSO_4$) and evaporated to yield the crude product. Purification by column chromatography (10 g of $SiO_2$, 2% methanol-chloroform) gave 33.8 mg (0.061 mmol, 31.4% yield) of compound 16 as an oil. $^1$H NMR ($CDCl_3$) δ 7.63 (1H, s), 7.03 (1H, s), 6.36 (1H, s), 5.23 (2H, s), 4.25 (1H, m), 5.14 (1H, d, J=8 Hz), 2.6–2.5 (2H, m), 2.24 (1H, m), 1.96 (1H, m), 1.48 (9H, s), 1.44 (9H, s); MS (ES, negative) 554.0, 556.0.

γ-(6-Bromo-7-hydroxycoumarin-4-yl)methyl glutamate (8).

A solution of 31.2 mg (0.0561 mmol) of compound 16 in dry $CH_2Cl_2$ (3 mL) and trifluoroacetic acid (1 mL) was stirred for 1 day at room temperature and evaporated to dryness. $^1$H NMR ($CD_3OD$) δ 7.84 (1H, s), 6.87 (1H, s), 6.30 (1H, s), 5.38 (2H, s), 4.09 (1H, dd, J=6.5 & 6.5 Hz), 2.81–2.70 (2H, m), 2.34–2.22 (2H, m); MS (ES, positive) 400.0 and 401.9; UV (KMOPS, pH 7.2) λmax (ε) 369 nm (19,550 $M^{-1}cm^{-1}$).

Chloromethylxanthene (25)

A mixture of 4.91 g (51.84 mmol) of chloroacetic acid, 4 mL (54.84 mmol) of thionyl chloride and one drop of DMF was stirred at 90° C. for 3 hours. The resulting solution was cooled and evaporated to remove excess thionyl chloride, hydrogen chloride and sulfur dioxide to yield crude chloroacetyl chloride as a colorless oil, pure enough to use in the next step without further purification. To a stirred suspension of 8.01 g (60.07 mmol) of anhydrous aluminum chloride in 10 mL of nitrobenzene were added 2 mL of chloroacetyl chloride and 2.37 g (21.52 mmol) of resorcinol at 0° C. The mixture was stirred at 0° C. for 10 minutes and at room temperature for 16 hours, poured into ice (ca. 20 mL), hydrolyzed by conc. HCl (10 mL), diluted with water (20 mL) and chloroform (50 mL) and separated. The organic layer was dried over MgSO4, evaporated and purified by column chromatography (75 g of $SiO_2$, 20% ethyl acetate-hexane) to yield 2.57 g (13.77 mmol, 64.0% yield) of 4-(2-chloroacetyl)resorcinol. A mixture of 167.2 mg (0.896 mmol) of 4-(2-chloroacetyl)resorcinol and 109.0 mg (0.990 mmol) of resorcinol in methanesulfonic acid (0.5 mL) was stirred at 85° C. for 1 hour. To the resulting deep red solution, ice (ca. 10 mL) was added to precipitate a product as a black gummy material which eventually became reddish brown fine powder after scratching with a spatula. The precipitate was collected by filtration, washed with water and dried over $P_2O_5$ under vacuum to yield 196.6 mg (0.754 mmol, 84% yield) of 9-chloromethylxanthene as a reddish brown solid. $^1$H NMR ($D_2O$+$K_2CO_3$) δ 7.66 (1H, d, J=9 Hz). 6.60 (1H, dd, J=9 & 2 Hz), 6.30 (1H, d, J=2 Hz), 4.82 (2H, s); MS (ES, positive) 261.4, 263.4; UV (KMOPS, pH 7.2) λmax (ε) 515 nm (41,200 $M^{-1}cm^{-1}$).

6-Bromo-7-hydroxy-4-methylcoumarin (17)

This compound was prepared by the method described for compound 25, yielding 453.1 mg (1.776 mmol, 49% yield) of compound 17.

6-Bromo-7-acetoxy-4-methylcoumarin (18)

To a solution of 453.1 mg (1.776 mmol) of compound 17 and 545 mL (3.9 mmol) of triethylamine in dry acetonitrile (5 mL) was added 255 mL (3.59 mmol) of acetyl chloride. The reaction mixture was stirred for 15 hours at room temperature, quenched with 1N HCl, diluted with chloroform and separated. The organic layer was washed with saturated aqueous $NaHCO_3$ and saturated aqueous brine, dried ($MgSO_4$) and evaporated to dryness to yield 404.9 mg (1.363 mmol, 76.7% yield) of the crude compound 18. This compound was used for the next reaction without a further purification.

6-Bromo-7-acetoxy-4-formylcoumarin (19)

A mixture of 404.9 mg (1.363 mmol) of compound 18, 239.2 mg (2.156 mmol) of selenium oxide in m-xylene (15 mL) was stirred under refluxed temperature for 21 hours. The reaction mixture was cooled and evaporated. Purification by column chromatography gave 287.0 mg (0.9226 mmol, 67.7% yield) of compound 19.

6-Bromo-7-acetoxy-4-formylcoumarin tosylhydrazone (20)

To a stirred solution of 101.8 mg (0.3273 mmol) of compound 19 in EtOH (4 mL) was added 61.6 mg (0.3308 mmol) of p-toluenesulfonylhydrazide. After 17 hours, the resulted precipitate was collected by filtration, washed and dried under vacuum to yield 103.2 mg (0.2153 mmol, 65.8% yield) of compound 20.

6-Bromo-7-acetoxy-4-diazomethylcoumarin (21)

A mixture of 103.2 mg (0.2153 mmol) of compound 20 and 45 mL (0.32 mmol) of triethylamine in MeOH (1.5 mL) was stirred at room temperature for 5.5 hours under a $N_2$ atmosphere. The resulting yellow precipitate was collected by filtration, washed with minimum amount of MeOH and dried under vacuum to yield 43.0 mg (0.133 mmol, 62% yield) of compound 21.

6-Bromo-7-hydroxy-4-diazomethylcoumarin (22)

A mixture of 43.0 mg (0.133 mmol) of compound 21 and 154.6 mg (2.36 mmol) of Zn in MeOH (10 mL) was stirred at room temperature for 75 hours under a $N_2$ atmosphere. Zn was removed by filtration and washed thoroughly with MeOH. The combined organic layer was evaporated to yield 37.5 mg (0.133 mmol, 100% yield) of compound 22. MS (ES, positive) 282.7, 284.7.

6-Bromo-7-hydroxycoumarin-4-ylmethyl diethylphosphate (23)

A mixture of 18.8 mg (66.9 mmol) of compound 22 and 100 mL of diethylphosphate in dry acetonitrile (1 mL) was stirred at room temperature for 24 hours under a $N_2$ atmosphere. The reaction mixture was evaporated and purified by column chromatography (15 g of $SiO_2$, 6% methanol-chloroform) to yield 7.6 mg (19 mmol, 28% yield) of compound 23. MS (ES, negative) 404.8, 406.7; UV (KMOPS, pH 7.2) λmax (ε) 368 nm (19,100 $M^{-1}cm^{-1}$).

6-Bromo-7-hydroxycoumarin-4-ylmethyl-cAMP (24)

A mixture of 14.6 mg (51.9 mmol) of 22 and 19.2 mg (58.3 mmol) of cAMP in dry dimethylsulfoxide (0.5 mL) was stirred at room temperature for 27 hours under a $N_2$ atmosphere. The reaction mixture was evaporated and purified by column chromatography (15 g of $SiO_2$, 9% methanol-chloroform then 33% methanol-chloroform) to yield 2.5 mg (4.3 mmol, 8.3% yield) of 24. MS (ES, negative) 582.0, 583.8.

EXAMPLE 2

One-photon Photolysis and Stability of Caged Compounds

The stability and photolytic properties of the caged compounds were measured. For comparison, the properties of four model compounds were also measured. The model compounds had the following structures:

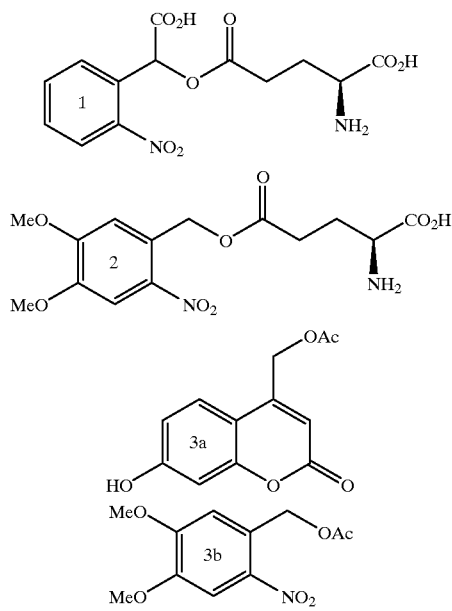

The compounds containing the photolabile protecting groups of the invention that were measured were:

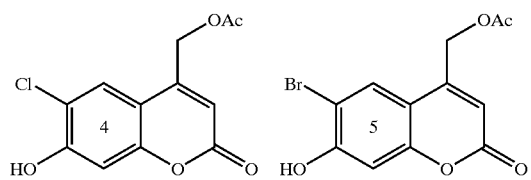

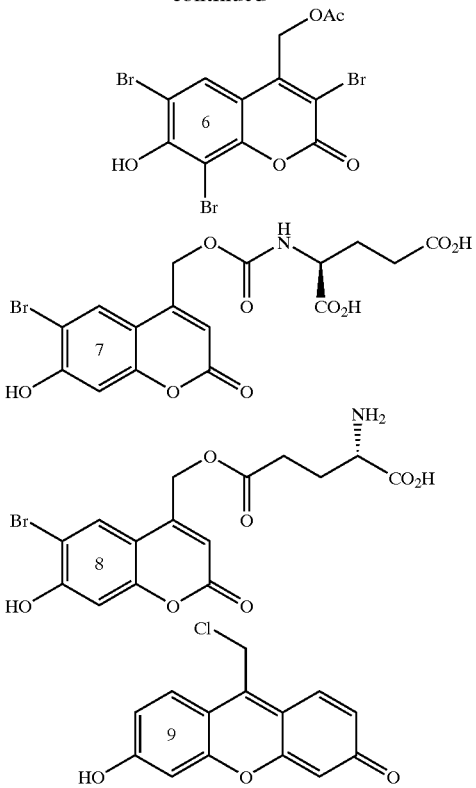

The electronic absorption and emission properties of the compounds were measured and the stability of the compounds toward hydrolysis in the dark was tested. Stability in the dark can be used to help identify photolabile protecting groups that can be used in a variety of different conditions. Specifically, the quantum efficiencies for one-photon excitation and rates of hydrolysis in the dark were determined.

The photolysis quantum efficiencies for one-photon excitation were determined by irradiating a buffered solution of the substrate with 365 nm ultraviolet light from a B-100 mercury lamp (Spectronics Corp., Westbury, N.Y.). The duration of each irradiation period was controlled by an electronic shutter. Between each irradiation, a small aliquot (10 μL) of the solution was removed for analysis by reversed phase HPLC with a Betabasic-18 column eluted with a isocratic mixture of 60% acetonitrile and water containing 0.1% trifluoracetic acid at a flow rate of 0.8 mL/min, using absorbance detection at 325 nm. Optical densities at 365 nm were maintained near 0.1 so that inner-filtering of the irradiation could be neglected. The hydrolysis progress curves exhibited simple exponential decay. Quantum efficiencies were calculated as $(I\sigma t_{90\%})^{-1}$, where I is the irradiation intensity in einsteins $(cm^{-2}s^{-1})$, σ is the decadic extinction coefficient in $cm^2mol^{-1}$ ($10^3$ times ε, the usual extinction coefficient in $M^{-1}cm^{-1}$), and $t_{90\%}$ is the irradiation time in seconds for 90% conversion to product. The total UV intensity, I, was measured by chemical actinometry with 6 mM potassium ferrioxalate in the same setup. Dark hydrolysis rates were measured similarly except without illumination. Selected data are summarized in Table I.

TABLE I

| Cmpd | $\epsilon^a$ | $\epsilon^b$ | $Q_{u1}^c$ | $\epsilon Q_{u1}^d$ | $Q_{f1}^e$ | $\lambda$em (nm) | $t_{0.5}$ (hr)$^f$ |
|---|---|---|---|---|---|---|---|
| 1 | 180 | | 0.14 | 25 | | | |
| 2 | 7,300 | 1,570 | 0.004 | 29 | | | |
| 3a | 4,100 | 1,000 | 0.025 | 103 | 0.20 | 474 | 202 |
| 3b | 5,200 | 1,300 | 0.005 | 26 | | | |
| 4 | 15,900 | 5,000 | 0.019 | 302 | 0.37 | 474 | 228 |
| 5 | 14,800 | 5,000 | 0.037 | 548 | 0.22 | 474 | 183 |
| 6 | 9,700 | 15,700 | 0.065 | 630 | 0.16 | 498 | 218 |
| 7 | 17,300 | 5,400 | 0.019 | 329 | 0.38 | 474 | |
| 8 | 19,200 | 7,560 | 0.019 | 364 | | | |
| 9$^g$ | 41,200 | | 0.038 | 1,565 | | 538 | |

$^a$Molar Absorptivity at 365 nm (M$^{-1}$cm$^{-1}$).
$^b$Molar Absorptivity at 400 nm (M$^{-1}$cm$^{-1}$).
$^c$Quantum efficiency for uncaging with one-photon excitation at 365 nm.
$^d$One-photon action cross section (product of molar absorptivity and photolysis quantum yield) at 365 nm (M$^{-1}$cm$^{-1}$).
$^e$Quantum efficiency for fluorescence with one-photon excitation.
$^f$Half-life for hydrolysis in the dark.
$^g\epsilon$ and $Q_{u1}$ measured at 515 nm rather than at 365 nm.

The photolysis products from compound 7 were analyzed. Specifically, glutamate released from compound 7 upon photolysis was quantified as its fluorescamine derivative by HPLC. For example, the production of glutamate from 100 μM 7 at pH 7.2 in KMOPS at 365 nm irradiation was as follows:

| Time | Yield (%) |
|---|---|
| 30 seconds | 27.6 |
| 60 seconds | 52.7 |
| 90 seconds | 74.5 |
| 120 seconds | 98.7 |

EXAMPLE 3

In Vitro Measurements of Two-photon Uncaging Cross-sections

Measurements of cross-sections for two-photon uncaging were carried out in microcuvettes with cylindrical cavities having a 1 cm path length and 20 μL total volume (Type 26F, Starna). Femtosecond infrared pulses from a mode-locked titanium-sapphire laser (Spectra-Physics TSUNAMI, pumped by a Spectra-Physics MILLENNIUM) were aimed along the axis of the sample chamber and focused in its center with a 25 mm focal length lens (06LXP003/076, Melles Griot, Irvine, Calif.) optimized for infrared lasers. The pulse parameters were estimated by replacing the caged compound by a solution of fluorescein, a reference compound of known fluorescence quantum yield $Q_{f2}$ (0.9) and two-photon absorbance cross-section $\delta_{aF}$ (30 and 38 GM at 740 and 800 nm respectively). The time-averaged fluorescence $<F(t)>$ collected by the detector is given by equation (1)

$$<F(t)>=0.5\phi Q_{f2}\delta_{aF}C_F<I_0^2(t)>\int S^2(r)dV \quad (1)$$

where φ is the collection efficiency of the detector, $C_F$ is the concentration of fluorescein, $<I_0^2(t)>$ is the mean squared light intensity, S(r) is a unitless spatial distribution function, and the integral is over the volume of the microcuvette. The fluorescence emitted at right angles to the laser beam was measured through a 535 nm bandpass filter in front of a silicon photodiode radiometer (IL1700, International Light). The collection efficiency φ was estimated as $A\gamma/(4\pi R^2 n^2)$, where A is the area of the detector (0.38 cm$^2$), γ is the fraction of the integrated emission spectrum transmitted by the interference filter (0.377), measured separately in a spectrofluorometer, R is the distance from the center of the cuvette to the detector (3.83 cm), and n is the refractive index of water (1.333). For photolysis of a caged compound or substrate, the number $N_P$ of molecules of product formed per unit time is (eq. 2):

$$N_P=0.5Q_{u2}\delta_{aS}C_S<I_0^2(t)>\int S^2(r)dV \quad (2)$$

where $Q_{u2}$, $\delta_{aS}$, and $C_S$ are the quantum efficiency for two-photon uncaging, absorbance cross-section, and concentration of the substrate, respectively. $N_P$ was measured by HPLC sampling of the microcuvette as for the one-photon photolysis. The uncaging action cross-section $\delta_{u2}$ ($\equiv Q_{u2}\delta_{aS}$) can therefore be estimated by (eq. 3):

$$\delta_{u2} = \frac{N_P \phi Q_{f2} \delta_{aF} C_F}{\langle F(t) \rangle C_S} \quad (3)$$

Similarly, when the substrate is also fluorescent, its two-photon fluorescence action cross-section $\delta_{f2S}$ ($\equiv Q_{f2S}\delta_{aS}$) can be estimated as (eq. 4):

$$\delta_{f2S} = \frac{\langle F(t) \rangle_S \phi_F C_F}{\langle F(t) \rangle_F \phi_S C_S} \delta_{f2F} \quad (4)$$

Here the subscripts S and F distinguish values for the substrate and for the fluorescein reference. If one assumes that one- and two-photon quantum efficiencies are the same, then $\delta_{u2}/Q_{u1}$ and $\delta_{f2S}/Q_{f1S}$ should both equal $\delta_{aS}$. In fact, the former values are typically about twice the latter. All of them are directly proportional to the assumed value of $Q_{f2}$ for fluorescein. The two-photon photolysis cross-section data are listed in Table II.

TABLE II

| Cmpd | $\lambda$max$^a$ | $\epsilon^b$ | $\delta_u$ (740 nm)$^c$ | $\delta_f$ (740 nm)$^d$ | $\delta_u$ (800 nm)$^e$ | $\delta_f$ (800 nm)$^f$ |
|---|---|---|---|---|---|---|
| 1 | | | | | | |
| 2 | 345 | 8,860 | | | | |
| 3a | 325 | 11,600 | 1.07 ± 0.05 | 3.85 ± 0.31 | 0.13 ± 0.01 | 1.26 ± 0.04 |
| 3b | 346 | 6,100 | 0.03 | | 0.01 | |
| 4 | 370 | 16,000 | 1.07 ± 0.07 | 9.68 ± 0.32 | 0.34 ± 0.02 | 3.22 ± 0.09 |
| 5 | 370 | 15,000 | 1.99 ± 0.09 | 4.24 ± 0.12 | 0.42 ± 0.01 | 1.41 ± 0.05 |
| 6 | 397 | 15,900 | 0.96 ± 0.05 | | 3.1 ± 0.2 | |
| 7 | 368 | 17,470 | 0.98 ± 0.24 | | 0.37 ± 0.06 | 2.2* |
| 8 | 369 | 19,550 | 0.89 ± 0.24 | | 0.42 ± 0.11 | |
| 9 | | | 1.6 | | 2.6 | 68 |

$^a$Wavelength of peak absorbance (nm); all measurements at pH 7.2.
$^b$Molar absorptivity at absorbance peak (M$^{-1}$cm$^{-1}$).
$^c\delta_u$ is the uncaging action cross-section in 10$^{-50}$ cm$^4$s/photon for two-photon excitation at 740 nm.
$^d\delta_f$ is fluorescence action cross-section in 10$^{-50}$ cm$^4$s/photon for two-photon excitation at 740 nm ($\delta_f = \delta_a Q_{f2}$, where $\delta_a$ is the absorbance cross-section and $Q_{f2}$ is the quantum efficiency for fluorescence, both with two-photon excitation).
$^e\delta_u$ is the uncaging action cross-section in 10$^{-50}$ cm$^4$s/photon for two-photon excitation at 800 nm.
$^f\delta_f$ is fluorescence action cross-section in 10$^{-50}$ cm$^4$s/photon for two-photon excitation at 800 nm ($\delta_f = \delta_a Q_{f2}$, where $\delta_a$ is the absorbance cross-section and $Q_{f2}$ is the quantum efficiency for fluorescence, both with two-photon excitation).
*Value measured at 780 nm on an independent apparatus.

The halogenated coumarin derivatives have good dark stability, and high one-photon and two-photon uncaging efficiencies. Without being bound to any particular theory, halogenation of the coumarin may have increased the two-photon cross-sections by lowering the $pK_a$ of the chromophore below physiological pH and promoting formation of the more strongly absorbing anion. Also, the heavy atoms may promote intersystem crossing to the triplet, which is believed to be the photochemically reactive state. Specifically, compounds 4–6 in Tables I and II show that two-photon cross-sections increased in the order 6-chloro<6-bromo<3,6,8-tribromo substitution. The mechanism of photolysis of compound 7 and compound 23 indicate that the solvolysis occurs via the triplet state with a lifetime of about 1 μs. The kinetics of glutamate release from compound 7 suggest that the initial release of the carbamic acid is unlikely to be rate-limiting. Although compound 6 had the highest cross-section, its photolysis was complicated by multiple secondary photoproducts. The monobromo compound (compound 5) was much more tractable and easily formed caged compounds. The γ-ester (compound 8) had a slightly higher two-photon cross-section than the carbamate (compound 7).

EXAMPLE 4

Uncaging Experiments

The photolabile protecting groups can be uncaged by one-photon or two-photon photolysis. A caged compound with the photolabile protecting groups of the invention can be used to deliver the compound to a sample, such as a biological sample, for example, brain slices, a spatially arrayed combinatorial library, or a three dimensional optical memory. Spatially arrayed combinatorial libraries are described, for example, in Pirrung, *Chem. Rev.* 197:473–488 (1997). Optical memories that employ a two-photon excitation is described, for example, in Strickler and Webb, *Optics Letters* 16:1780–1782 (1991).

The photolabile protecting groups can be uncaged by one-photon or two-photon photolysis. One-photon ultraviolet uncaging experiments were carried out on brain slices. In particular, compound 7 was used to deliver glutamate to rat cortical neurons. One-photon UV uncaging of caged glutamate compound at 365 nm released the glutamate. Neuronal responses were measured after directly stimulating cells as described in Sawatari and Callaway, *Nature* 380:442–446 (1996). The cells were exposed to compound 7 (Bhc-Glu) or γ-(α-carboxy-2-nitrobenzyl)glutamate, trifluoroacetate salt (compound 1, CNB-glutamate). The one-photon uncaging was carried out as described in FIG. 1 depicts the lower power needed to uncage compound 7 (Bhc-Glu) in the neuron sample in comparison to compound 1 (alpha-carboxy nitrobenzyl-caged glutamate, CNB-Glu). At 10 mW the compound 7-stimulated neurons respond, on average, at amplitudes 80% of their maximum, while compound 1-stimulated neurons are responding at less than 20% of their maximum amplitudes.

In addition, two-photon uncaging experiments can yield additional information because of the low degree of damage caused in the sample by high-power infrared pulses used to uncage the compound. For example, the caged glutamate compounds allowed nondestructive three-dimensional mapping of the glutamate responsivity over the surface of a neuron to be carried out. A map was created where the brightness at each picture element was proportional to the maximum current recorded with the laser focused at that position. The resulting map of the neuronal responsivity to glutamate looked like a fuzzy fluorescence image of the outer surface of the cell. It was fuzzier because photolysis a short distance away from the cell still produced a response because glutamate diffused after uncaging. The photolysis map was intrinsically different from the image of an intracellular fluorescent marker because the photolysis map highlights the locations of the most electrically-active glutamate receptors. For example, the inside of the cell was dark in the photolysis map, because the Bhc-glutamate did not enter the cell, and even if it did, intracellularly released glutamate cannot activate the receptors on the outside of the cell. Thus, when the plane of laser scanning cuts through the center of the cell body, the photolysis shows a bright ring with a dark center.

Two-photon infrared uncaging on brain slices was also carried out. A central property of two-photon excitation is the elimination of out-of-focus background (see, Denk, W., et al., *Science* 248:73–76 (1990)). Two-photon uncaging allowed the production of glutamate only in the plane of focus, following the procedure described in Denk, W., *Proc. Natl. Acad. Sci. USA* 91:6629–6633 (1994). Carbamate compound 7 was applied to slices and the presence of the compound was monitored directly using its fluorescence at low levels of two-photon excitation. During whole-cell recordings, application of compound 7 did not cause detectable changes in holding current (15 cells), showing that this compound lacks intrinsic agonist activity. The stream of pulses from the Ti:sapphire laser was raster-scanned across cell bodies and dendrites. In the absence of caged compound, scans caused no changes in holding current (15 cells). After application of compound 7, scans evoked inward currents having an amplitude that was strongly dependent on beam power. The peak current amplitude increased as a supra-linear function of beam power, mostly caused by the nonlinear power dependence expected for a two-photon process (see, Pettit, D. L., et al., *Neuron* 19:465–471 (1997), and Denk, W., et al., *Science* 248:73–76 (1990)).

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and, without departing from the spirit and scope thereof, can make various changes and modifications of the invention to adapt it to various usages and conditions. Thus, other embodiments are also within the claims.

What is claimed is:

1. A compound of formula

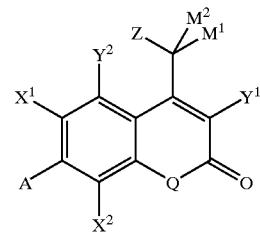

wherein:
A is —OH, —OC(O)CH$_3$, NH$_2$, or —NHCH$_3$;
each of X$^1$ and X$^2$, independently, is H, Cl, Br, or I, with at least one of X$^1$ and X$^2$ being Cl, Br, or I;

Q is —O—, —NH—, or —NCH$_3$—;

Y$^1$ is —H, —Cl, —Br, —I, —C(O)OH, —NO$_2$, —C(O)NHR$^1$, —CN, —C(O)H, —C(O)CH$_3$, benzoxazol-2-yl, benzothiazol-2-yl, or benzimidazol-2-yl;

Y$^2$ is —H, —C(O)OH, or —SO$_3$H;

M$^1$ is —H, —CH$_3$, —NR$^2$R$^3$, —C(O)NR$^2$R$^3$, or —COOH;

Z is —Cl, —Br, —I—, —OH, —OC(O)R$^4$, —OP(O)R$^5$R$^6$ and M$^2$ is —H;

or Z and M$^2$ together are =N$_2$, =O, or =NNHR$^1$;

each of R$^1$, R$^2$, and R$^3$, independently, is a substituted or unsubstituted moiety selected from the group consisting of a C$_{1-20}$ alkyl, a C$_{2-20}$ alkenyl, a C$_{2-20}$ alkynyl, a C$_{1-20}$ alkoxy, a C$_{1-20}$ thioalkoxy, a C$_{1-20}$ alkylsulfonyl, a C$_{4-16}$ arylsulfonyl, a C$_{2-20}$ heteroalkyl, a C$_{2-20}$ heteroalkenyl, a C$_{3-8}$ cycloalkyl, a C$_{3-8}$ cycloalkenyl, a C$_{4-16}$ aryl, a C$_{4-16}$ heteroaryl, and a C$_{2-30}$ heterocyclyl; and each of R$^4$, R$^5$, and R$^6$ independently, is a substituted or unsubstituted moiety selected from the group consisting of a C$_{1-20}$ alkyl, a C$_{2-20}$ alkenyl, a C$_{4-16}$ aryl, a C$_{2-20}$ heteroalkyl, an amino acid radical, a peptide radical, a polynucleotide radical, and a nucleoside radical or R$^5$ and R$^6$ together can form a nucleoside diradical;

or a salt thereof.

2. The compound of claim 1, wherein:

A is —OH, or —OC(O)CH$_3$;

each of X$^1$ and X$^2$, independently, is H, Cl, Br, or I, with at least one of X$^1$ and X$^2$ being Cl, Br, or I;

Q is —O—;

Y$^1$ is —H;

Y$^2$ is —H;

M$^1$ is —H or —CH$_3$;

Z is —OH, —OC(O)R$^4$, —O$_3$SR$^4$, —OP(O)R$^5$R$^6$ and M$^2$ is —H;

or Z and M$^2$ together are =N$_2$ or NNHR$^1$;

R$^1$ is a C$_{4-16}$ arylsulfonyl; and each of R$^4$, R$^5$, and R$^6$ independently, is a substituted or unsubstituted moiety selected from the group consisting of a C$_{1-20}$ alkyl, a C$_{2-20}$ alkenyl, a C$_{4-16}$ aryl, a C$_{2-20}$ heteroalkyl, an amino acid radical, a peptide radical, a polynucleotide radical, and a nucleoside radical;

or R$^5$ and R$^6$ together can form a nucleoside diradical.

3. The compound of claim 2, wherein:

A is —OH;

each of X$^1$ and X$^2$, independently, is H, Cl, Br, or I, with at least one of X$^1$ and X$^2$ being Cl, Br, or I;

Q is —O—;

Y$^1$ is —H;

Y$^2$ is —H;

M$^1$ is —H or —CH$_3$;

Z is —OC(O)R$^4$; and

R$^4$ is a substituted or unsubstituted moiety selected from the group consisting of a C$_{2-20}$ heteroalkyl, a C$_{2-20}$ alkenyl, an amino acid radical and a peptide radical.

4. The compound of claim 3, wherein:

A is —OH;

X$^1$ is Br;

X$^2$ is H;

Q is —O—;

Y$^1$ is —H;

Y$^2$ is —H;

M$^1$ is —H;

Z is —OC(O)R$^4$; and

R$^4$ is an amino acid radical or a C$_{2-20}$ heteroalkyl.

5. The compound of claim 4, wherein R$^4$ is —NH—CH(COOH)—CH$_2$CH$_2$COOH.

6. The compound of claim 4, wherein R$^4$ is —NHCH$_2$CH$_2$CH$_2$COOH.

7. The compound of claim 4, wherein R$^4$ is —CH$_2$CH$_2$-CH(COOH)-NH$_2$.

8. The compound of claim 4, wherein R$^4$ is —CH$_2$CH$_2$CH$_2$NH$_2$.

9. The compound of claim 3, wherein:

A is —OH;

X$^1$ is Br;

X$^2$ is H;

Q is —O—;

Y$^1$ is —H;

Y$^2$ is —H;

M$^1$ is —H;

Z is —OC(O)R$^4$; and

R$^4$ is a C$_{2-20}$ alkenyl.

10. The compound of claim 9, wherein R$^4$ is —(CH$_2$)$_7$—CH=CH—CH$_2$—CH=CH—CH$_2$—CH=CH—CH$_2$—CH$_3$.

11. The compound of claim 2, wherein:

A is —OH, or —OC(O)CH$_3$;

each of X$^1$ and X$^2$, independently, is H, Cl, Br, or I, with at least one of X$^1$ and X$^2$ being Cl, Br, or I;

Q is —O—;

Y$^1$ is —H;

Y$^2$ is —H;

M$^1$ is —H or —CH$_3$; and

Z and M$^2$ together are =N$_2$ or NNHR$^1$; and

R$^1$ is a C$_{4-16}$ arylsulfonyl.

12. The compound of claim 11, wherein:

A is —OH;

X$^1$ is Br;

X$^2$ is H;

Q is —O—;

Y$_1$ is —H;

Y$^2$ is —H;

M$^1$ is —H; and

Z and M$^2$ together are =N$_2$.

13. The compound of claim 11, wherein:

A is —OC(O)CH$_3$;

X$^1$ is Br;

X$^2$ is H;

Q is —O—;

Y$^1$ is —H;

Y$^2$ is —H;

M$^1$ is —H; and

Z and M$^2$ together are NNHR$^1$; and

R$^1$ is a C$_{4-16}$ arylsulfonyl.

14. The compound of claim 13, wherein:
A is —OC(O)CH$_3$;
X$^1$ is Br;
X$^2$ is H;
Q is —O—;
Y$^1$ is —H;
Y$^2$ is —H;
M$^1$ is —H; and
Z and M$^2$ together are NNHR$^1$; and
  R$^1$ is

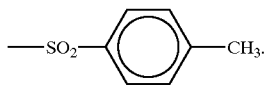

15. The compound of claim 11, wherein:
A is —OC(O)CH$_3$;
X$^1$ is Br;
X$^2$ is H;
Q is —O—;
Y$^1$ is —H;
Y$^2$ is —H;
M$^1$ is —H; and
Z and M$^2$ together are =N$_2$.

16. The compound of claim 2, wherein:
A is OH;
X$^1$ is Br;
X$^2$ is H;
Q is —O—;
Y$^1$ is —H;
Y$^2$ is —H;
M$^1$ is —H;
M$^2$ is —H; and
Z is —OP(O)R$^5$R$^6$ and
  each of R$^5$ and R$^6$ independently is a polynucleotide radical, or
  R$^5$ and R$^6$ together is a nucleoside diradical.

17. The compound of claim 16, wherein:
A is OH;
X$^1$ is Br;
X$^2$ is H;
Q is —O—;
Y$^1$ is —H;
Y$^2$ is —H;
M$^1$ is —H;
M$^2$ is —H; and
Z is —OP(O)R$^5$R$^6$ and
R$^5$ R$^6$ together are

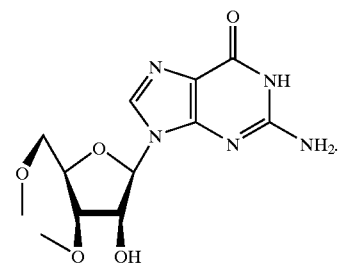

18. The compound of claim 16, wherein:
A is OH;
X$^1$ is Br;
X$^2$ is H;
Q is —O—;
Y$^1$ is —H;
Y$^2$ is —H;
M$^1$ is —H;
M$^2$ is —H; and
Z is —OP(O)R$^5$R$^6$ and
  R$^5$ and R$^6$ together are

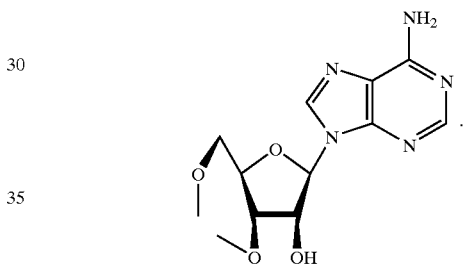

19. The compound of claim 16, wherein:
A is OH;
X$^1$ is Br;
X$^2$ is H;
Q is —O—;
Y$^1$ is —H;
Y$^2$ is —H;
M$^1$ is —H;
M$^2$ is —H;
Z is —OP(O)R$^5$R$^6$;
  R$^5$ is a 3' polynucleotide radical; and
  R$^6$ is a 5' polynucleotide radical.

* * * * *